US012702548B2

(12) United States Patent
Nir et al.

(10) Patent No.: US 12,702,548 B2
(45) Date of Patent: Aug. 11, 2026

(54) LEAFLET ATTACHMENT IN PROSTHETIC HEART VALVES USING BUCKLE COMMISSURE CLAMPS

(71) Applicant: Edwards Lifesciences Corporation, Irvine, CA (US)

(72) Inventors: Noam Nir, Pardes-Hanna (IL); Michael Bukin, Pardes Hanna (IL)

(73) Assignee: Edwards Lifesciences Corporation, Irvine, CA (US)

( * ) Notice: Subject to any disclaimer, the term of this patent is extended or adjusted under 35 U.S.C. 154(b) by 800 days.

(21) Appl. No.: 17/978,826

(22) Filed: Nov. 1, 2022

(65) Prior Publication Data

US 2023/0051890 A1 Feb. 16, 2023

Related U.S. Application Data

(63) Continuation of application No. PCT/US2021/030423, filed on May 3, 2021.
(Continued)

(51) Int. Cl.
*A61F 2/24* (2006.01)
*A61F 2/30* (2006.01)

(52) U.S. Cl.
CPC .......... *A61F 2/2418* (2013.01); *A61F 2/2409* (2013.01); *A61F 2002/30177* (2013.01);
(Continued)

(58) Field of Classification Search
None
See application file for complete search history.

(56) References Cited

U.S. PATENT DOCUMENTS 3,409,013 A 11/1968 Berry
3,548,417 A 12/1970 Ronnie et al.
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Tan-Uyen T Ho
(74) *Attorney, Agent, or Firm* — Klarquist Sparkman, LLP

(57) ABSTRACT

A buckle commissure clamp can be used to attach leaflets of a valvular structure to a frame of a prosthetic heart valve. Tabs of adjacent leaflets can be assembled to the buckle commissure clamp by passing each leaflet through one or more gaps of the buckle commissure clamp. Each leaflet tab can be wrapped around portions of the buckle commissure clamp. Once the leaflet tabs are assembled to the buckle commissure clamp, the assembly can be attached to the frame, for example, by one or more sutures extending between the buckle commissure clamp and a support member, such as a strut of the frame, an actuator of the frame, a locking mechanism of the frame. In some embodiments, the buckle commissure clamp has a substantially W-shape or M-shape.

19 Claims, 8 Drawing Sheets

Related U.S. Application Data

(60) Provisional application No. 63/019,596, filed on May 4, 2020.

(52) U.S. Cl.
CPC ................ *A61F 2220/0075* (2013.01); *A61F 2250/0069* (2013.01)

(56) References Cited

U.S. PATENT DOCUMENTS

| | | | |
|---|---|---|---|
| 3,587,115 | A | 6/1971 | Donald |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| RE30,912 | E | 4/1982 | Hancock |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goicoechea et al. |
| 6,338,740 | B1 | 1/2002 | Carpentier |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,979 | B2 | 3/2003 | Constantz et al. |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,096,554 | B2 | 8/2006 | Austin et al. |
| 7,225,518 | B2 | 6/2007 | Eidenschink et al. |
| 7,276,078 | B2 | 10/2007 | Spenser et al. |
| 7,276,084 | B2 | 10/2007 | Yang et al. |
| 7,316,710 | B1 | 1/2008 | Cheng et al. |

(56) References Cited

U.S. PATENT DOCUMENTS

| | | | |
|---|---|---|---|
| 7,318,278 | B2 | 1/2008 | Zhang et al. |
| 7,374,571 | B2 | 5/2008 | Pease et al. |
| 7,393,360 | B2 | 7/2008 | Spenser et al. |
| 7,462,191 | B2 | 12/2008 | Spenser et al. |
| 7,510,575 | B2 | 3/2009 | Spenser et al. |
| 7,563,280 | B2 | 7/2009 | Anderson et al. |
| 7,585,321 | B2 | 9/2009 | Cribier |
| 7,618,446 | B2 | 11/2009 | Andersen et al. |
| 7,618,447 | B2 | 11/2009 | Case et al. |
| 7,655,034 | B2 | 2/2010 | Mitchell et al. |
| 7,785,366 | B2 | 8/2010 | Maurer et al. |
| 7,959,665 | B2 | 6/2011 | Pienknagura |
| 7,959,672 | B2 | 6/2011 | Salahieh et al. |
| 7,993,394 | B2 | 8/2011 | Hariton et al. |
| 8,029,556 | B2 | 10/2011 | Rowe |
| 8,075,611 | B2 | 12/2011 | Millwee et al. |
| 8,128,686 | B2 | 3/2012 | Paul et al. |
| 8,167,932 | B2 | 5/2012 | Bourang et al. |
| 8,291,570 | B2 | 10/2012 | Eidenschink et al. |
| 8,348,998 | B2 | 1/2013 | Pintor et al. |
| 8,449,606 | B2 | 5/2013 | Eliasen et al. |
| 8,454,685 | B2 | 6/2013 | Hariton et al. |
| 8,652,203 | B2 | 2/2014 | Quadri et al. |
| 8,685,055 | B2 | 4/2014 | VanTassel et al. |
| 8,747,463 | B2 | 6/2014 | Fogarty et al. |
| 9,078,781 | B2 | 7/2015 | Ryan et al. |
| 11,224,509 | B2 | 1/2022 | Dasi et al. |
| 2001/0021872 | A1 | 9/2001 | Bailey et al. |
| 2002/0026094 | A1 | 2/2002 | Roth |
| 2002/0032481 | A1 | 3/2002 | Gabbay |
| 2002/0138135 | A1 | 9/2002 | Duerig et al. |
| 2002/0143390 | A1 | 10/2002 | Ishii |
| 2002/0173842 | A1 | 11/2002 | Buchanan |
| 2003/0014105 | A1 | 1/2003 | Cao |
| 2003/0040791 | A1 | 2/2003 | Oktay |
| 2003/0050694 | A1 | 3/2003 | Yang et al. |
| 2003/0100939 | A1 | 5/2003 | Yodfat et al. |
| 2003/0158597 | A1 | 8/2003 | Quiachon et al. |
| 2003/0212454 | A1 | 11/2003 | Scott et al. |
| 2004/0024452 | A1 | 2/2004 | Kruse et al. |
| 2004/0039436 | A1 | 2/2004 | Spenser et al. |
| 2004/0078074 | A1 | 4/2004 | Anderson et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0010285 | A1 | 1/2005 | Lambrecht et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0096738 | A1 | 5/2005 | Cali et al. |
| 2005/0137686 | A1 | 6/2005 | Salahieh et al. |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0108090 | A1 | 5/2006 | Ederer et al. |
| 2006/0149350 | A1 | 7/2006 | Patel et al. |
| 2006/0183383 | A1 | 8/2006 | Asmus et al. |
| 2006/0229719 | A1 | 10/2006 | Marquez et al. |
| 2006/0259136 | A1 | 11/2006 | Nguyen et al. |
| 2006/0259137 | A1 | 11/2006 | Artof et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0112422 | A1 | 5/2007 | Dehdashtian |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2008/0021546 | A1 | 1/2008 | Patz et al. |
| 2008/0114442 | A1 | 5/2008 | Mitchell et al. |
| 2008/0125853 | A1 | 5/2008 | Bailey et al. |
| 2008/0154355 | A1 | 6/2008 | Benichou et al. |
| 2008/0183271 | A1 | 7/2008 | Frawley et al. |
| 2008/0208327 | A1 | 8/2008 | Rowe |
| 2008/0243245 | A1 | 10/2008 | Thambar et al. |
| 2008/0255660 | A1 | 10/2008 | Guyenot et al. |
| 2008/0275537 | A1 | 11/2008 | Limon |
| 2008/0294248 | A1 | 11/2008 | Yang et al. |
| 2009/0118826 | A1 | 5/2009 | Khaghani |
| 2009/0125118 | A1 | 5/2009 | Gong |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0299452 | A1 | 12/2009 | Eidenschink et al. |
| 2009/0319037 | A1 | 12/2009 | Rowe et al. |
| 2010/0004735 | A1 | 1/2010 | Yang et al. |
| 2010/0049313 | A1 | 2/2010 | Alon et al. |
| 2010/0082094 | A1 | 4/2010 | Quadri et al. |
| 2010/0100176 | A1 | 4/2010 | Elizondo et al. |
| 2010/0168844 | A1 | 7/2010 | Toomes et al. |
| 2010/0185277 | A1 | 7/2010 | Braido et al. |
| 2010/0198347 | A1 | 8/2010 | Zakay et al. |
| 2010/0204781 | A1 | 8/2010 | Alkhatib |
| 2011/0015729 | A1 | 1/2011 | Jimenez et al. |
| 2011/0022157 | A1 | 1/2011 | Essinger et al. |
| 2011/0066224 | A1 | 3/2011 | White |
| 2011/0137397 | A1 | 6/2011 | Chau et al. |
| 2011/0218619 | A1 | 9/2011 | Benichou et al. |
| 2011/0319991 | A1 | 12/2011 | Hariton et al. |
| 2012/0030090 | A1 | 2/2012 | Johnston et al. |
| 2012/0089223 | A1 | 4/2012 | Nguyen et al. |
| 2012/0101571 | A1 | 4/2012 | Thambar et al. |
| 2012/0123529 | A1 | 5/2012 | Levi et al. |
| 2012/0259409 | A1 | 10/2012 | Nguyen et al. |
| 2013/0023985 | A1 | 1/2013 | Khairkhahan et al. |
| 2013/0046373 | A1 | 2/2013 | Cartledge et al. |
| 2013/0150956 | A1 | 6/2013 | Yohanan et al. |
| 2013/0166017 | A1 | 6/2013 | Cartledge et al. |
| 2013/0190857 | A1 | 7/2013 | Mitra et al. |
| 2013/0274873 | A1 | 10/2013 | Delaloye et al. |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0222136 | A1 | 8/2014 | Geist et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |
| 2014/0277563 | A1 | 9/2014 | White |
| 2014/0296962 | A1 | 10/2014 | Cartledge et al. |
| 2014/0330372 | A1 | 11/2014 | Weston et al. |
| 2014/0343670 | A1 | 11/2014 | Bakis et al. |
| 2014/0343671 | A1 | 11/2014 | Yohanan et al. |
| 2014/0350667 | A1 | 11/2014 | Braido et al. |
| 2015/0073545 | A1 | 3/2015 | Braido |
| 2015/0073546 | A1 | 3/2015 | Braido |
| 2015/0135506 | A1 | 5/2015 | White |
| 2015/0157455 | A1 | 6/2015 | Hoang et al. |
| 2016/0374802 | A1 | 12/2016 | Levi et al. |
| 2017/0014229 | A1 | 1/2017 | Nguyen-Thien-Nhon et al. |
| 2018/0028310 | A1 | 2/2018 | Gurovich et al. |
| 2018/0153689 | A1 | 6/2018 | Maimon et al. |
| 2018/0325665 | A1 | 11/2018 | Gurovich et al. |
| 2018/0344456 | A1 | 12/2018 | Barash et al. |
| 2019/0076245 | A1 | 3/2019 | Arcaro et al. |
| 2019/0159894 | A1 | 5/2019 | Levi et al. |

(56) References Cited

U.S. PATENT DOCUMENTS

| | | | |
|---|---|---|---|
| 2019/0192288 | A1 | 6/2019 | Levi et al. |
| 2019/0192289 | A1 | 6/2019 | Levi et al. |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | B1 | 5/1988 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| EP | 3563803 | A1 | 11/2019 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

LEAFLET ATTACHMENT IN PROSTHETIC HEART VALVES USING BUCKLE COMMISSURE CLAMPS

CROSS-REFERENCE TO RELATED APPLICATION

This application is a continuation of a PCT Application No. PCT/US2021/030423, entitled "Leaflet Attachment in Prosthetic Heart Valves Using Buckle Commissure Clamps," filed May 3, 2021, which claims the benefit of U.S. Provisional Application No. 63/019,596, entitled "Leaflet Attachment in Prosthetic Heart Valves Using Buckle Commissure Clamps," filed May 4, 2020, wherein each of the above-referenced is incorporated by reference herein in its entirety.

FIELD

The present disclosure relates to prosthetic heart valves, and to methods and assemblies for attaching leaflets to frames of such prosthetic heart valves using buckle commissure clamps.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size. Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Expandable, transcatheter heart valves can comprise an annular metal frame or stent and prosthetic leaflets mounted inside the frame. Leaflet tabs can be wrapped around and sutured to commissure posts of the frame. However, such commissure tab assemblies may be relatively complex and time-consuming to assemble. In addition, attachment of the leaflet tabs to the commissure post may be subject to undesirable wear along the numerous stitches required. Moreover, when the commissure post has a non-circular cross-section, e.g., a rectangular post, wrapping of the leaflet tabs around the post may result in a relatively loose attachment.

SUMMARY

Described herein are embodiments of prosthetic heart valves and methods for assembling prosthetic heart valves. In some embodiments, a pair of tabs of adjacent leaflets of a valvular structure for the prosthetic heart valve are pre-assembled to a buckle commissure clamp. In some embodiments, the leaflet tabs can follow respective serpentine paths through gaps in the buckle commissure clamp and can wrap around respective portions of the buckle commissure clamp. In some embodiments, free ends of the tabs can be secured to each other or to one or more coupling members on a side of the buckle commissure clamp opposite the valvular structure. In some embodiments, the assembly of leaflet tabs and buckle commissure clamp can then be attached to an expandable annular frame of the heart valve. For example, one or more sutures can couple the buckle commissure clamp to a post, actuator, or locking member of the annular frame.

In one representative embodiment, an assembly method for a prosthetic heart valve comprises providing a buckle commissure clamp, and coupling tabs of adjacent leaflets to the buckle commissure clamp by passing each leaflet through one or more gaps of the buckle commissure clamp such that each leaflet tab is wrapped around at least a respective portion of the buckle commissure clamp. The leaflets can form a part of a valvular structure for the prosthetic heart valve.

In another representative embodiment, a prosthetic heart valve can comprise an expandable frame, a plurality of buckle commissure clamps, and a valvular structure. The buckle commissure clamps can be coupled to the frame. Each buckle commissure clamp can have one or more gaps. The valvular structure can be formed by a leaflet assembly that comprises a plurality of leaflets. Each leaflet can have a pair of tabs. Each leaflet tab can be coupled to a respective one of the buckle commissure clamps by being wrapped around at least a portion of the buckle commissure clamp.

In another representative embodiment, a preassembly comprises a plurality of buckle commissure clamps and a valvular structure. Each buckle commissure clamp can have one or more gaps. The valvular structure can be formed by a leaflet assembly that comprises a plurality of leaflets. Each leaflet can have a pair of tabs. Each leaflet tab can be coupled to a respective one of the buckle commissure clamps by being wrapped around at least a portion of the buckle commissure clamp. The preassembly can subsequently be attached to a frame of a prosthetic heart valve.

Any of the various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosed technology will become more apparent from the following detailed description, which proceeds with reference to the accompanying figures.

DETAILED DESCRIPTION

General Considerations

Figure 1:
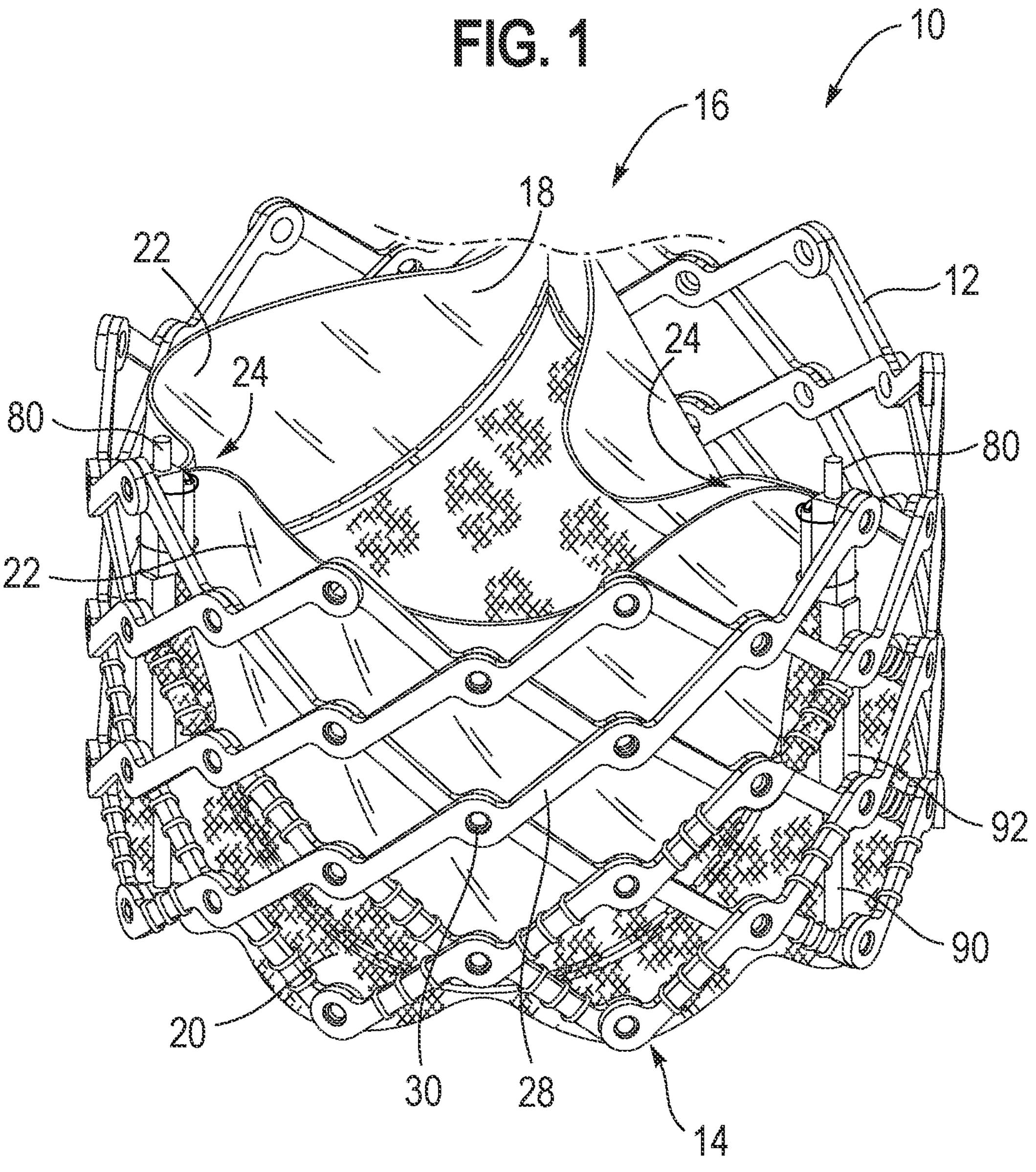
FIG. 1 is a perspective view of an exemplary mechanically expandable prosthetic heart valve.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved. The technologies from any example can be combined with the technologies described in any one or more of the other examples.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like “provide” or “achieve” to describe the disclosed methods. These terms are high-level abstractions of the actual operations that are performed. The actual operations that correspond to these terms may vary depending on the particular implementation and are readily discernible by one of ordinary skill in the art.

As used herein with reference to the prosthetic heart valve assembly and implantation and structures of the prosthetic heart valve, “proximal” refers to a position, direction, or portion of a component that is closer to the user and a handle of the delivery system or apparatus that is outside the patient, while “distal” refers to a position, direction, or portion of a component that is further away from the user and the handle, and closer to the implantation site. The terms “longitudinal” and “axial” refer to an axis extending in the proximal and distal directions, unless otherwise expressly defined.

The terms “axial direction,” “radial direction,” and “circumferential direction” have been used herein to describe the arrangement and assembly of components relative to the geometry of the frame of the prosthetic heart valve. Such terms have been used for convenient description, but the disclosed embodiments are not strictly limited to the description. In particular, where a component or action is described relative to a particular direction, directions parallel to the specified direction as well as minor deviations therefrom are included. Thus, a description of a component extending along an axial direction of the frame does not require the component to be aligned with a center of the frame; rather, the component can extend substantially along a direction parallel to a central axis of the frame.

As used herein, the terms “integrally formed” and “unitary construction” refer to a construction that does not include any welds, fasteners, or other means for securing separately formed pieces of material to each other.

As used herein, operations that occur “simultaneously” or “concurrently” occur generally at the same time as one another, although delays in the occurrence of operation relative to the other due to, for example, spacing between components, are expressly within the scope of the above terms, absent specific contrary language.

As used in this application and in the claims, the singular forms “a,” “an,” and “the” include the plural forms unless the context clearly dictates otherwise. Additionally, the term “includes” means “comprises.” Further, the term “coupled” generally means physically, mechanically, chemically, magnetically, and/or electrically coupled or linked and does not exclude the presence of intermediate elements between the coupled or associated items absent specific contrary language. As used herein, “and/or” means “and” or “or,” as well as “and” and “or.”

Directions and other relative references may be used to facilitate discussion of the drawings and principles herein, but are not intended to be limiting. For example, certain terms may be used such as “inner,” “outer,” “upper,” “lower,” “inside,” “outside,”, “top,” “bottom,” “interior,” “exterior,” “left,” “right,” and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an “upper” part can become a “lower” part simply by turning the object over. Nevertheless, it is still the same part and the object remains the same.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term “about.” Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods, as known to those of ordinary skill in the art. When directly and explicitly distinguishing embodiments from discussed prior art, the embodiment numbers are not approximates unless the word "about" is recited. Whenever "substantially," "approximately," "about," or similar language is explicitly used in combination with a specific value, variations up to and including 10% of that value are intended, unless explicitly stated otherwise.

Examples of the Disclosed Technology

Described herein are examples of prosthetic heart valves, frames with commissure support posts and leaflet assemblies for prosthetic heart valves, and methods for assembling leaflet assemblies to commissure support posts of frames to form prosthetic heart valves. The prosthetic heart valve may include an expandable frame and a valvular structure formed by a leaflet assembly supported by the frame. The leaflets can be coupled to the frame via a plurality of buckle commissure clamps. Tabs of adjacent leaflets are passed through one or more gaps of a buckle commissure clamp and wrapped around one or more portions of the buckle commissure clamp in order to secure the leaflets to the clamp. Free ends of the leaflet tabs can be further secured, for example, by directly coupling together (e.g., stitching via one or more sutures) or by attachment to a coupling member extending between the free ends. The buckle commissure clamp can be secured to the frame, for example, by one or more sutures wrapped around portions of the clamp and corresponding portions of a support member, which may be a strut of the frame, an actuator, a locking member, or another member coupled thereto. Frictional forces between the wrapped leaflet tabs and the portions of the buckle commissure clamp can be sufficient to retain the leaflets in position once installed to the prosthetic heart valve, thereby minimizing, or at least reducing, forces experienced by or required for the stitched free ends.

FIG. 1 shows an exemplary prosthetic heart valve 10, according to one or more embodiments of the disclosed subject matter. The prosthetic heart valve 10 can be radially compressible and expandable between a radially compressed configuration for delivery into a patient and a radially expanded configuration (as shown in FIG. 1). In particular embodiments, the prosthetic heart valve 10 can be implanted within the native aortic annulus, although it can also be implanted at other locations in the heart, including within the native mitral valve, the native pulmonary valve, or the native tricuspid valve, or within a prosthetic heart valve previously implanted at any of the aforementioned valve positions (e.g., a valve-in-valve procedure).

The prosthetic heart valve 10 can include a frame 12 (e.g., a substantially annular stent) having a first axial end 14 and a second axial end 16. In the depicted embodiment, the first axial end 14 can be an inflow end, and the second axial end 16 can be an outflow end. The outflow end 16 can be coupled to a delivery apparatus for delivering and implanting the prosthetic heart valve within the native aortic valve is a transfemoral, retrograde delivery approach. Thus, in the delivery configuration of the prosthetic heart valve, the outflow end 16 is the proximal-most end of the prosthetic valve. In other embodiments, the inflow end 14 can be coupled to the delivery apparatus, depending on the particular native valve being replaced and the delivery technique that is used (e.g., trans-septal, transapical, etc.). For example, the inflow end 14 can be coupled to the delivery apparatus (and therefore would be the proximal-most end of the prosthetic heart valve in the delivery configuration) when delivering the prosthetic heart valve to the native mitral valve via a trans-septal delivery approach.

As shown in FIG. 1, frame 12 can include a plurality of interconnected struts 28 arranged in a lattice-type pattern. The struts 28 are shown as positioned diagonally, or offset at an angle relative to, and radially offset from, a longitudinal axis of the prosthetic heart valve 10 when the prosthetic heart valve 10 is in the expanded configuration. In other implementations, the struts 28 can be offset by a different amount than depicted in FIG. 1, or some or all of the struts 28 can be positioned parallel to the longitudinal axis of the prosthetic heart valve 10.

In the embodiment illustrated in FIG. 1, the struts 28 are pivotably coupled to one another at one or more pivot joints along the length of each strut. For example, each of the struts 28 can be formed with apertures at opposing ends of the strut and apertures spaced along the length of the strut. Respective hinges can be formed at the locations where struts 28 overlap each other via fasteners or pivot members, such as fasteners 30 (e.g., rivets or pins) that extend through the apertures. The hinges can allow the struts 28 to pivot relative to one another as the frame 12 is radially expanded or compressed, such as during assembly, preparation, or implantation of the prosthetic heart valve 10. The frame 12, or components thereof (e.g., struts 28 and/or fasteners 30), can be made of any of various suitable materials, such as stainless steel, a cobalt chromium alloy, or a nickel titanium alloy ("NiTi"), for example Nitinol.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube, such as a hypotube). Further details regarding construction of the frame and the prosthetic heart valve are described in U.S. Patent Application Publication Nos. 2018/0153689, 2018/0344456, 2019/0060057, 2020/0188099, and 2020/0390547, and International Application Publication No. WO-2020/081893, all of which are incorporated herein by reference.

The prosthetic heart valve 10 can further include a plurality of actuators 80 mounted to and spaced around an inner surface of the frame 12. The actuators can be configured to apply corresponding expansion and compression forces to the frame in order to radially expand or compress the prosthetic valve. For example, in the illustrated embodiment, the actuators 80 are linear actuators, each of which comprises an inner member 90 (e.g., piston) and an outer member 92 (e.g., cylinder). The inner member 90 is pivotably coupled to a junction of the frame, such as at the first axial end 14, while the outer member 92 is pivotably coupled to another junction of the frame closer to the second axial end 16. Moving the inner member 90 proximally relative to the outer member 92 and/or moving the outer member 92 distally relative to the inner member 90 can be effective to radially expand the prosthetic valve. Conversely, moving the inner member 90 distally relative to the outer member 92 and/or moving the outer member 92 proximally relative to the inner member 90 can be effective to radially compress the prosthetic valve. The actuators 80 can include locking mechanisms that are configured to retain the prosthetic valve in an expanded state inside the patient's body.

In some embodiments, each of the actuators 80 can be configured to form a releasable connection with one or more respective actuators of a delivery apparatus of a transcatheter delivery system. The actuators of the delivery apparatus can transmit forces from a handle of the delivery apparatus to the actuators 80 for expanding or compressing the prosthetic valve. Further details of the actuators, locking mechanisms and delivery apparatuses for actuating the actuators can be found in U.S. Patent Application Publication Nos. 2018/0153689, 2018/0325665, and 2019/0060057, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

In some embodiments, each of the actuators 80 can be used to support a respective commissure 24 formed by adjacent tabs of a pair of leaflets 22. As such, the actuators 80 can include support members for supporting and securing commissures 24 of a valvular structure 18 to the frame 12. For example, the support member may be a portion of the actuator 80 or its locking mechanism, or it may be a separate structure coupled to the actuator 80 or its locking mechanism. Alternatively or additionally, the frame 12 of the heart valve 10 can include support members as separate structures from the actuators 80. For example, the commissures 24 can be mounted to support members that are support struts or posts of the frame 12 that are separate from the actuators 80. In such a configuration, the support members may be referred to as commissure posts or commissure locking posts. In some embodiments, the support members (or a subsection thereof to which the commissures 24 are coupled) may be substantially aligned with, or extend along a direction substantially parallel to, the longitudinal axis of the frame 12.

The prosthetic heart valve 10 can also include a valvular structure 18, which is coupled to the frame 12 and configured to regulate the flow of blood through the prosthetic heart valve 10 from the inflow end 14 to the outflow end 16. The valvular structure 18 can include, for example, a leaflet assembly formed by one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). Further details regarding transcatheter prosthetic heart valves, including the manner in which the valvular structure can be coupled to the frame 12 of the prosthetic heart valve 10, can be found, for example, in U.S. Pat. Nos. 6,730,118, 7,393,360, 7,510,575, 7,993,394, and 8,652,202, and U.S. Patent Application Publication No. 2018/0325665, all of which are incorporated herein by reference in their entireties.

The prosthetic heart valve 10 can also include one or more skirts or sealing members. For example, as shown in FIG. 1, the prosthetic heart valve 10 can include an inner skirt 20 mounted on the inner surface of the frame 12. As shown in FIG. 1, the inner skirt 20 is a circumferential inner skirt that spans an entire circumference of the inner surface of the frame 12. The inner skirt 20 can function as a sealing member to prevent or decrease perivalvular leakage (e.g., when the valve is placed at the implantation site) and as an attachment surface to anchor the leaflets 22 to the frame 12.

The prosthetic heart valve 10 can also include an outer skirt mounted on the outer surface of the frame 12 (not shown in FIG. 1). The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

Figure 2:
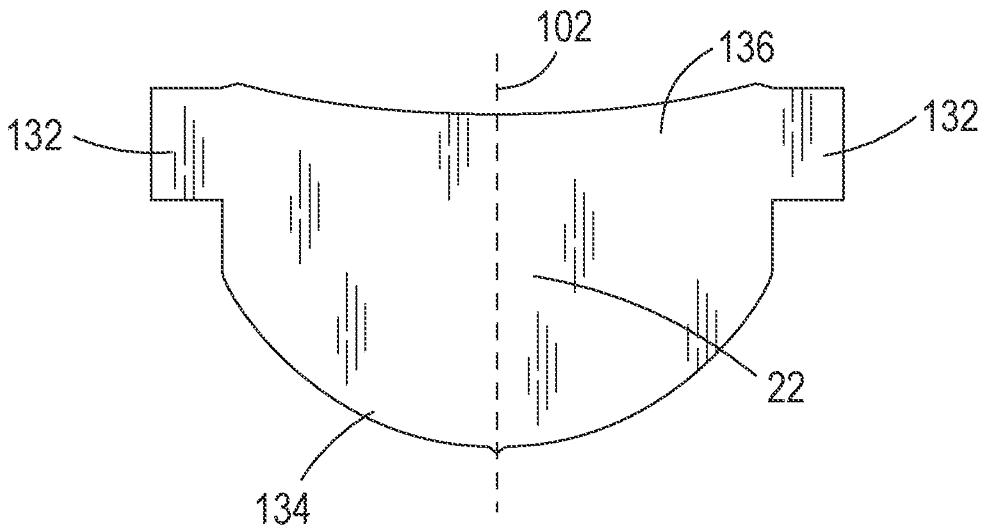
FIG. 2 is a plan view of an individual leaflet used to form a leaflet assembly for a prosthetic heart valve.

As shown in FIG. 2, each leaflet 22 can comprise a main, cusp edge portion 134, two leaflet tabs 132 at opposing ends of the cusp edge portion 134, and an upper edge portion 136. The cusp edge portion 134, leaflet tabs 132, and upper edge portion 136 may be arranged around an outer perimeter of the leaflet 22, with the upper edge portion 136 extending between the two leaflet tabs 132 at an upper edge of the leaflet 22 and the cusp edge portion 134 extending between the two leaflet tabs 132 at a lower edge of the leaflet 22. As used here, "upper" and "lower" may be relative to a central longitudinal axis of the prosthetic heart valve 10 when the leaflet assembly is installed and coupled to frame 12 of the prosthetic heart valve 10.

In some embodiments, the cusp edge portion 134 has a curved, scalloped shape (as shown in FIG. 2). Thus, the cusp edge portion 134 may curve between the two leaflet tabs 132. FIG. 2 further illustrates a centerline 102 for each of the individual leaflets 22, which may also be a centerline of the leaflet assembly. For example, when assembled, the centerlines 102 for each of the leaflets 22 may overlap. Further, as shown in FIG. 2, the leaflet tabs 132 may be arranged at opposing ends of the cusp edge portion 134, across the centerline 102 from one another. In some embodiments, the leaflets and/or components of the leaflet assembly may have symmetry with respect to the centerline 102.

Figure 3A:
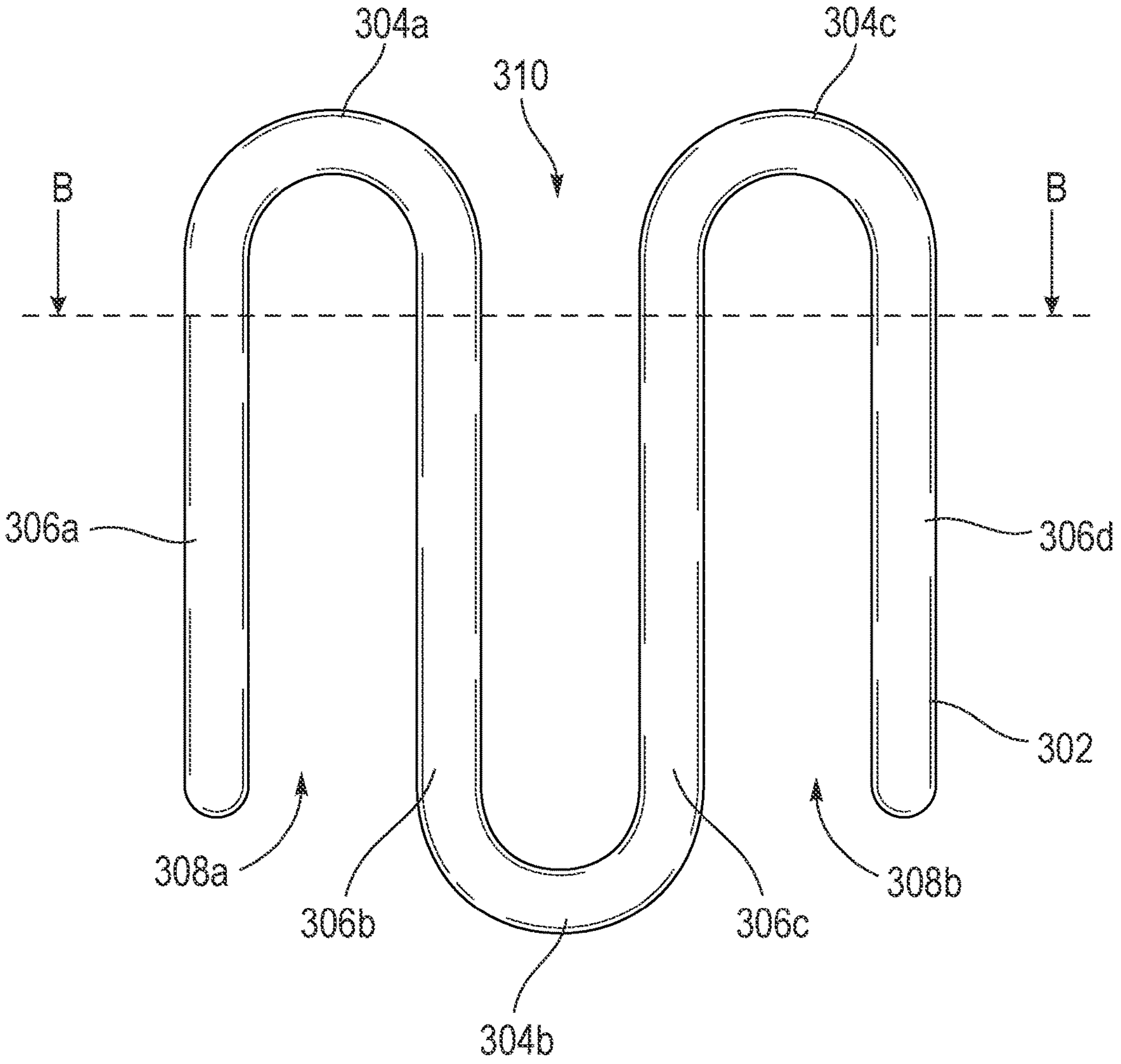
FIGS. 3A-3B are side and cross-sectional views, respectively, of an exemplary buckle commissure clamp.
Figure 3B:
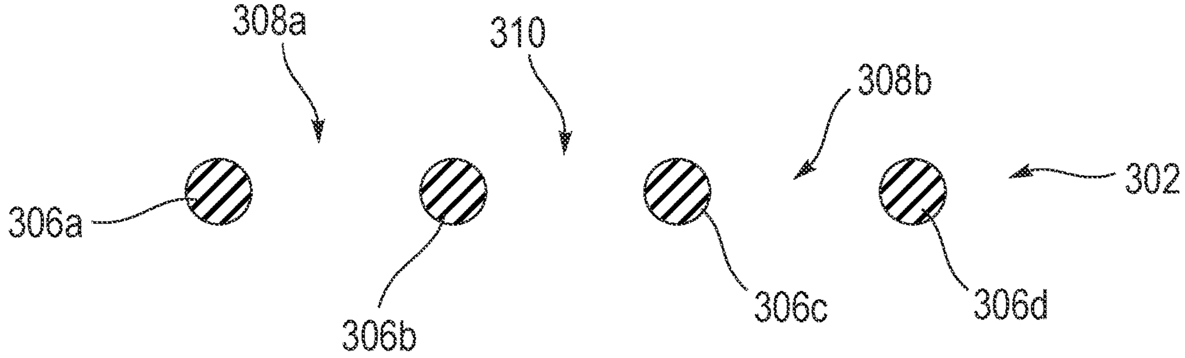

In some embodiments, the commissures 24, which are formed by leaflet tabs 132 of adjacent leaflets 22, are pre-assembled to a buckle commissure clamp. The assembly of commissures 24 with the buckle commissure clamp can then be mounted to the support member, for example, by one or more sutures. For example, FIGS. 3A-3B show an exemplary embodiment of a buckle commissure clamp 302, to which a commissure 24 can be pre-assembled. In the illustrated embodiment, the buckle commissure clamp 302 has an undulating profile as viewed from the side, for example, having an M-shape (e.g., upside-down W-shape), that defines multiple gaps or recesses, through which portions of the leaflet tabs may be passed to secure the commissure to the clamp. Alternatively, the buckle commissure clamp 302 can have a W-shape, for example, by rotating the structure illustrated in FIG. 3A by 180°.

Buckle commissure clamp 302 can include a pair of outer end portions, e.g., first end portion **306*a* and second end portion 306*d*, and a pair of inner arms, e.g., first arm 306*b* and second arm 306*c*. The first end portion 306*a* and the first arm 306*b* are connected to each other at a top end of the buckle commissure clamp 302 by a curved member, e.g., a first bent portion 304*a*. Similarly, the second end portion 306*d* and the second arm 306*c* are connected to each other at the top end of the buckle commissure clamp 302 by another curved member, e.g., a second bent portion 304*c*. The inner arms 306*b*, 306*c* are connected to each other at a bottom end of the buckle commissure clamp 302 by yet another curved member, e.g., a third bent portion 304*b***.

In some embodiments, the end portions 306*a*, 306*d* and the inner arms 306*b*, 306*c* may be substantially coplanar (e.g., portions/arms 306*a*-306*d* disposed along a common line in cross-section, as shown in FIG. 3B). Alternatively or additionally, the end portions 306*a*, 306*d* and the inner arms 306*b*, 306*c* are substantially parallel to each other. For example, the end portions 306*a*, 306*d* may be substantially coplanar with each other, while inner arms 306*b*, 306*c* may also be substantially coplanar with each other but offset from the end portions 306*a*, 306*d* in the cross-sectional view of FIG. 3B. In some embodiments, end portions 306*a*, 306*d* and inner arms 306*b*, 306*c* may be substantially straight members. For example, end portions 306*a*, 306*d* and inner arms 306*b*, 306*c* may each extend along a respective direction that is parallel to an axial direction of the prosthetic heart valve. Alternatively, in some embodiments, each of the portions/arms 306*a*-306*d* are angled with respect to one, some, or all of the other of the portions/arms 306*a*-306*d*.

In some embodiments, the buckle commissure clamp 302 can be formed of a single member bent or otherwise formed (e.g., molding, casting, machining, etc.) into the configuration illustrated in FIGS. 3A-3B. For example, the clamp 302 can be formed by bending a flexible straight rod or wire, e.g., a wire formed of a metal or metal alloy, such as stainless steel, titanium, or any other biocompatible metal material. Although a circular cross-section is illustrated in FIG. 3B, other cross-sectional shapes are also possible according to one or more embodiments. In some embodiments, all surfaces, or at least some surfaces (e.g., those surfaces that contact leaflet tabs 132*a*, 132*b*) are designed as smooth surfaces so as to minimize, or at least reduce, the likelihood of abrasion due to contact with the leaflets. For example, smooth surfaces of the clamp 302 contacting the leaflets may be substantially flat or curved without any edges or projections. Alternatively or additionally, smooth surfaces of the clamp 302 may have a relatively low surface roughness. In some embodiments, the buckle commissure clamp 302 can include a coating (e.g., polymer layer) to enhance the surface smoothness or friction properties thereof.

For example, the buckle commissure clamp 302 can be formed by bending a straight metal wire about its center to from the bent portion 304*b*. The resulting U-shaped structure of the bent wireform can be further subject to additional bending, first to form one of bent portions 304*a*, 304*c* and then to form the other of bent portions 304*a*, 304*c*. For example, the first bent portion 304*a* can be formed at a midpoint between an end of first end portion 306*a* and the central bent portion 304*b*. Similarly, the second bent portion 304*c* can be formed at a midpoint between an end of second end portion 306*d* and the central bent portion 304*b*. Locations for the first and second bent portions 304*a*, 304*c* other than the aforementioned midpoints are also possible according to one or more contemplated embodiments.

The buckle commissure clamp 302 can thus form multiple gaps or recesses, in particular, central gap 310 that opens to the top end of the clamp 302 and a pair of outer gaps that open to the bottom end of the clamp 302, e.g., left gap 308*a* and right gap 308*b*. The central gap 310 can be defined by the inner arms 306*b*, 306*c* and the third bent portion 304*b*. The left gap 308*a* can be defined by the first end portion 306*a*, the first arm 306*b*, and the first bent portion 304*a*, while the right gap 308*b* can be defined by the second end portion 306*d*, the second arm 306*c*, and the second bent portion 304*c*.

Figure 4A:
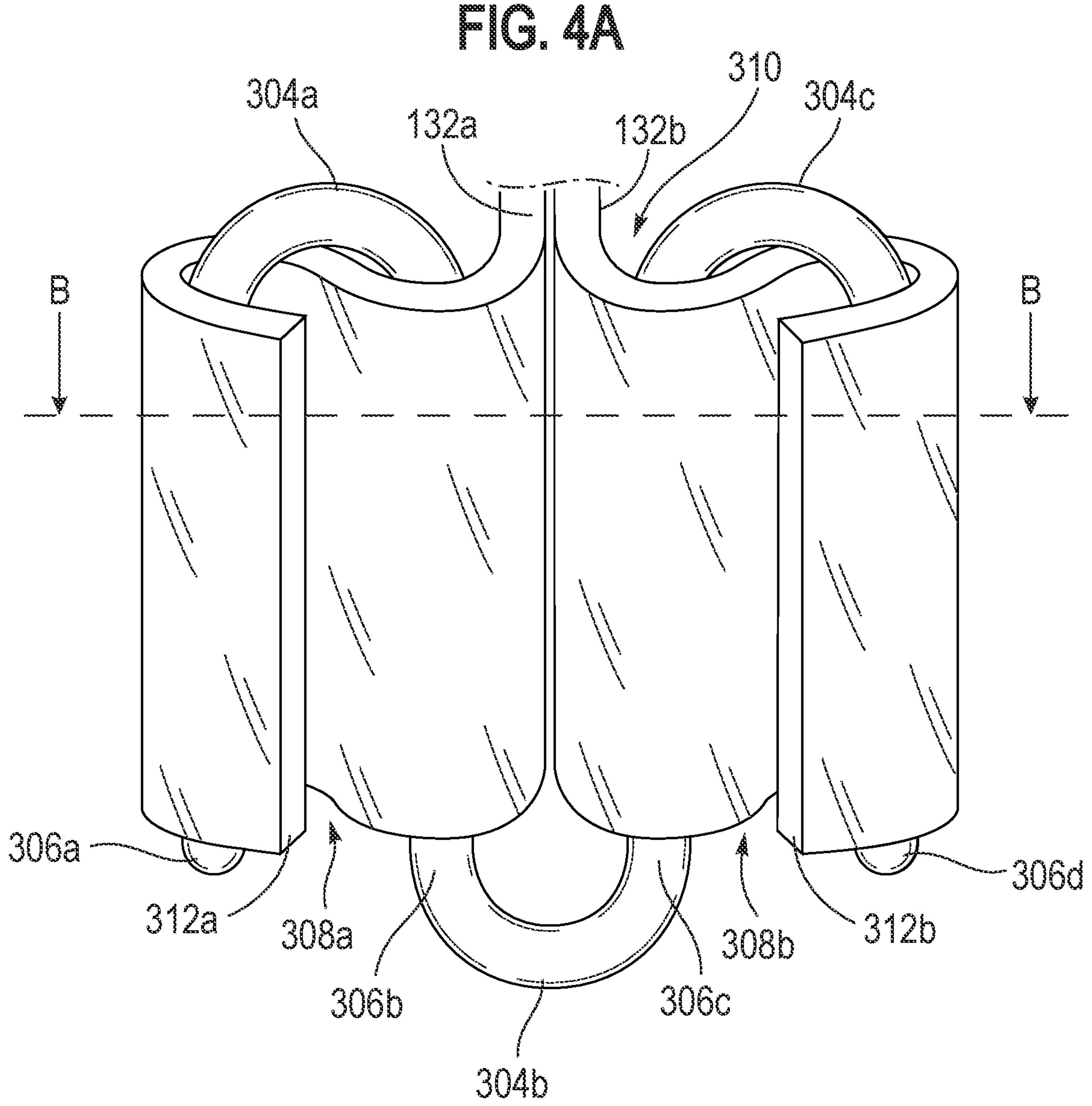
FIGS. 4A-4B are side and cross-sectional views, respectively, of a pair of leaflet tabs assembled to the buckle commissure clamp of FIGS. 3A-3B.
Figure 4B:
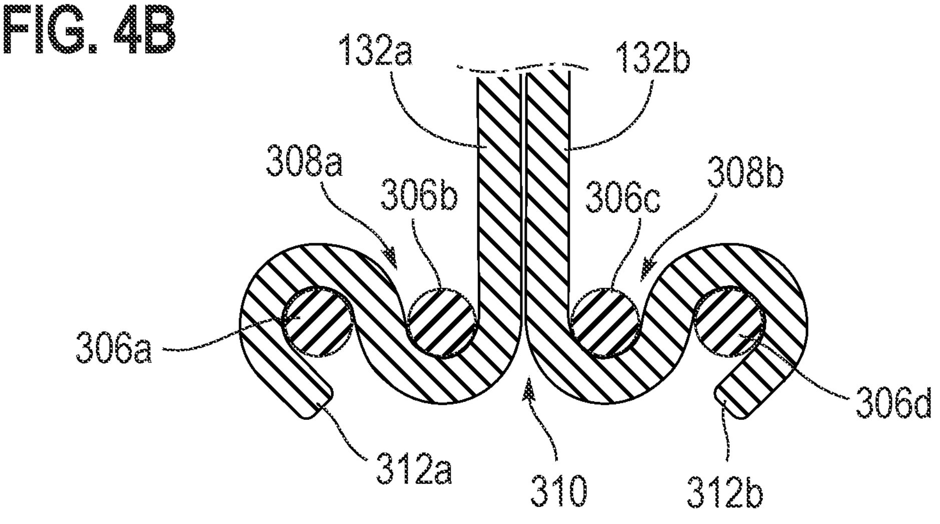

To secure the commissures 24 of adjacent leaflets to the buckle commissure clamp 302, each leaflet tab 132 can be inserted through the gaps of the clamp 302 by following a serpentine path around portions of the clamp 302. For example, as shown in FIGS. 4A-4B, a pair of adjacent leaflet tabs 132*a*, 132*b* can be inserted into the central gap 310. In some embodiments, the pair of adjacent leaflet tabs 132*a*, 132*b* can be inserted through the central gap 310 simultaneously. For example, the pair of leaflet tabs 132*a*, 132*b* can be positioned together and then inserted into the central gap 310 as a unit. Alternatively, each leaflet tab 132*a*, 132*b* can be separately inserted into the central gap 310. For example, one of the leaflet tabs 132*a*, 132*b* can be inserted into the gap 310, after which the other of the leaflet tabs 132*a*, 132*b* can be inserted into the gap 310. In another example, one of the leaflet tabs 132*a*, 132*b* can be inserted into the gap 310 and positioned along its serpentine path through other respective gaps of the clamp 302 to its final disposition, after which the other of the leaflet tabs 132*a*, 132*b* can be inserted into the gap 310 and positioned along its serpentine path.

In some embodiments, the insertion of leaflet tabs 132*a*-132*b* into the central gap 310 is along a first direction from a first side of the buckle commissure clamp 302 to a second side of the clamp 302. When installed within the frame of the prosthetic heart valve, the second side of the clamp 302 may be disposed farther from a center of the frame than the first side of the clamp 302, and thus the second side of the clamp 302 may be considered the radially outer side. Alternatively or additionally, leaflet tabs 132*a*-132*b* can be inserted into the central gap 310 by sliding through the open end of the gap 310, e.g., along a second direction from the first end of the buckle commissure clamp 302 toward a second end of the clamp 302. When installed within the frame of the prosthetic heart valve, the first end of the buckle commissure clamp 302 may be disposed closer to the outflow end 16 of the valve than the second end of the clamp. Thus, the first end of the clamp 302 may be considered the proximal end, while the second end of the clamp 302 may be considered the distal end. However, in some embodiments, the clamp 302 can be turned 180° (e.g., having a W-configuration rather than the M configuration of FIG. 4A) or the inflow end 14 of valve 10 can be coupled to a delivery apparatus, in which case, the first end of the clamp 302 may be considered the distal end, while the second end of the clamp 302 may be considered the proximal end.

After insertion into the central gap 310, each leaflet tab 132*a*, 132*b* is further secured to the buckle commissure clamp 302 by following a serpentine path through gaps of the clamp 302, so as to wrap around multiple portions of the clamp 302. For example, the portion of the left leaflet tab 132*a* that extends through central gap 310 to the second side of the clamp 302 can be folded over first arm 306*b* and inserted through left gap 308*a* to the first side of the clamp 302. The remaining portion of the left leaflet tab 132*a* that extends through left gap 308*a* can be further folded over first end portion 306*a* and passed from the first side of the clamp 302 back to the second side of the clamp 302. Similarly, the portion of the right leaflet tab 132*b* that extends through central gap 310 to the second side of the clamp 302 can be folded over second arm 306*c* and inserted through right gap 308*b* to the first side of the clamp 302. The remaining portion of the right leaflet tab 132*b* that extends through right gap 308*b* can be further folded over second end portion 306*d* and passed from the first side of the clamp 302 back to the second side of the clamp 302. The free ends 312*a*, 312*b* of leaflet tabs 132*a*, 132*b* are thus disposed on the second side of the clamp 302 (e.g., at respective locations between the first end portion 306*a* and the second end portion 306*d*) and can be secured to each other, for example, as described in further detail below.

The disposition of the leaflet tabs 132*a*, 132*b* along their respective serpentine paths through central gap 310 and outer gaps 308*a*, 308*b* of the clamp 302 allows the leaflet tabs 132*a*, 132*b* to contact surfaces of the clamp 302 at multiple locations. For example, left leaflet tab 132*a* can wrap around and be in contact with at least a portion of the first arm 306*b* and at least a portion of the first end portion 306*a*. Similarly, right leaflet tab 132*b* can wrap around and be in contact with at least a portion of the second arm 306*c* and at least a portion of the second end portion 306*d*. In some embodiments, surface areas of the inner arms 306*b*, 306*c* covered by the respective leaflet tab 132*a*, 132*b* is less than surface areas of the end portions 306*a*, 306*d* covered by the respective leaflet tab 132*a*, 132*b*. The winding paths and the distributed surface contact can yield frictional forces sufficient to secure the leaflets to the buckle commissure clamp. This can reduce the amount of forces required at the free end 312*a*, 312*b* of the leaflet tabs, for example, via sutures or other attachment means.

In some embodiments, once the leaflet tabs 132*a*, 132*b* have been woven through gaps of the buckle commissure clamp 302 and have their free ends 312*a*, 312*b* disposed on the second side of the clamp 302, the free ends 312*a*, 312*b* can be secured to each other using one or more coupling members. Alternatively, in some embodiments, one of the free ends (e.g., left free end 312*a*) can be attached to one or more of the coupling members 314*a*, 314*b* before the corresponding other leaflet (e.g., right leaflet 132*b*) is inserted through its corresponding outer gap (e.g., gap 308*b*).

Figure 5A:
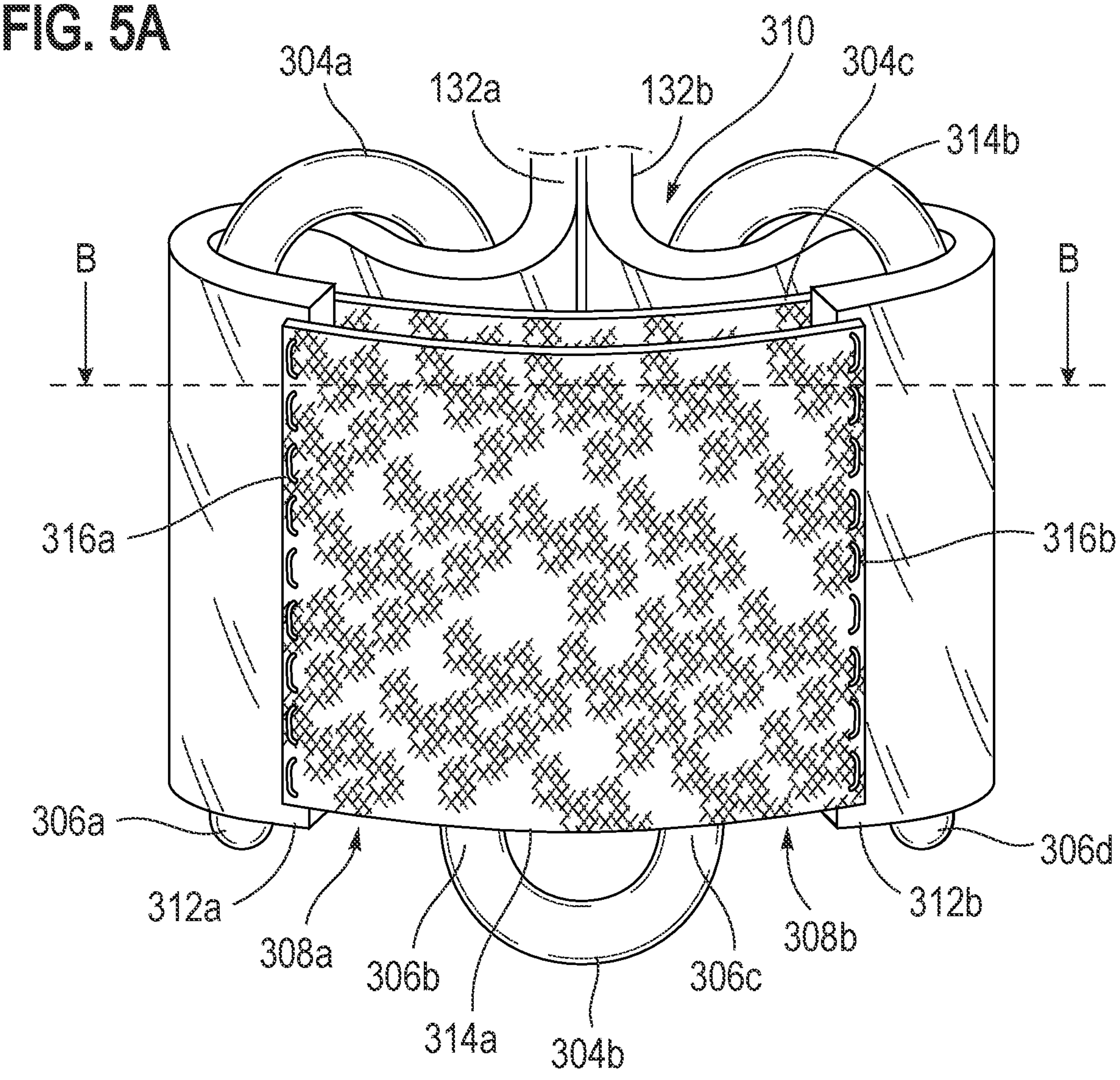
FIGS. 5A-5B are side and cross-sectional views, respectively of an exemplary option for securing free ends of the leaflet tabs assembled to the buckle commissure clamp using a pair of coupling members.
Figure 5B:
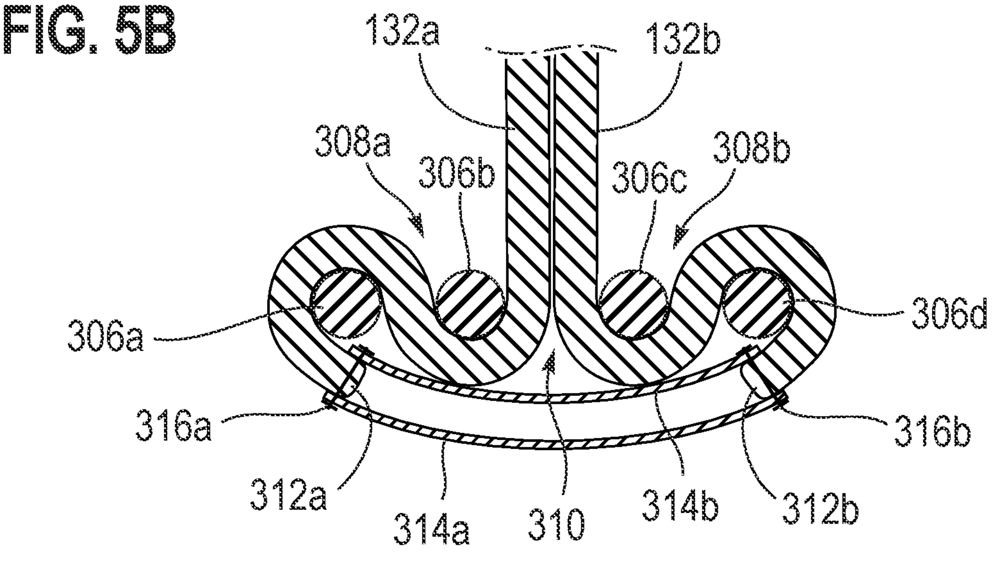

For example, as shown in FIGS. 5A-5B, a pair of coupling members 314*a*, 314*b* can extend between and contact free ends 312*a*, 312*b*. For example, each coupling member 314*a*, 314*b* may be a flexible cloth or fabric strip. A first coupling member 314*b* can be disposed between free ends 312*a*, 312*b* and clamp 302 along the first direction from the first side to the second side of the clamp 302. A second coupling member 314*a* can then be disposed on an opposite side of the free ends 312*a*, 312*b* from the first coupling member 314*b*, such that the free ends 312*a*, 312*b* are sandwiched along the first direction between facings portions of the coupling members 314*a*, 314*b*, as shown in FIG. 5B.

The left ends of coupling members 314*a*, 314*b* can be coupled to free end 312*a* of left leaflet tab 132*a*, while the right ends of coupling members 314*a*, 314*b* can be coupled to free end 312*b* of right leaflet tab 132*b*. For example, the ends of the coupling members 314*a*, 314*b* and free ends 312*a*, 312*b* can be coupled together by stitching, e.g., sutures 316*a* that extend through the coupling members 314*a*, 314*b* at one end with free end 312*a* sandwiched therebetween, and sutures 316*b* that extend through the coupling members 314*a*, 314*b* at the opposite end with free end 312*b* sandwiched therebetween. Alternatively or additionally, the coupling members and leaflet tabs can be coupled together via other attachment means, such as, but not limited to, using an adhesive.

In some embodiments, the assembly of the leaflet tabs 132*a*, 132*b* with the buckle commissure clamp 302 can further include one or more wedge elements disposed at the second side of the buckle commissure clamp 302. Each wedge element can be formed from a relatively thick multi-filament or monofilament polymer suture, yarn or cable (e.g., a braided, polyester suture, such as an Ethibond suture), a piece of cloth or fabric folded one or more times to increase its thickness, or any other structure. For example, the disclosed wedge elements can be formed of a material that does not encourage tissue ingrowth, such as ultra-high molecular weight polyethylene (UHMPE), polyethylene terephthalate (PET), polyurethane (PU), or polytetrafluoroethylene (PTFE). Alternatively or additionally, any other material that is minimally porous, configured to prevent or minimize neo-vascularization, or does not allow tissue anchoring can be used for the disclosed wedge elements. Alternatively or additionally, the disclosed wedge elements can be a coated or laminated polymeric material. In some embodiments, the material for the disclosed wedge elements can be a polymer material that is processed in a manner, or otherwise configured, to reduce the likelihood for tissue ingrowth. For example, if exposure of the material to certain levels of heat may induce thrombogenicity, the materials for the disclosed wedge elements may be processed in a manner that avoids or reduces such heating steps.

Figure 5C:
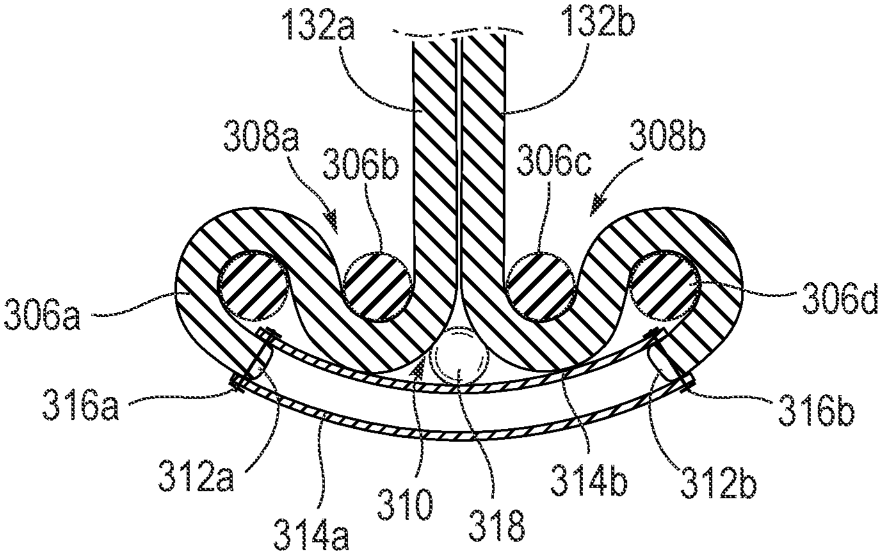
FIG. 5C illustrates a cross-sectional view of another exemplary option for securing free ends of the leaflet tabs assembled to the buckle commissure clamp using a pair of coupling members and a wedge.

For example, FIG. 5C illustrates a wedge element 318 arranged between the splayed portions of tabs 132*a*, 132*b* extending through central gap 310 and the first coupling member 314*b*. The wedge element 318, which is adjacent to central gap 310, may be in contact with the leaflet tabs 132*a*, 132*b* and first coupling member 314*b*. In some embodiments, the wedge element 318 may apply a biasing force to further push portions of the leaflet tabs into contact with inner arms 306*b*, 306*c*. For example, when the assembly of leaflet tabs and buckle commissure clamp is installed in the prosthetic heart valve, support member can push against the wedge element 118 via coupling members 314*a*, 314*b* to further urge the wedge element 118 against the splayed leaflet portions 132*a*, 132*b* extending through central gap 310.

In some embodiments, the wedge element 318 can be inserted as a final step in forming the assembly of leaflets to the buckle commissure clamp 302. For example, the wedge element 318 can be inserted along the second direction (i.e., from the first end to the second end of the clamp 302, which may be substantially parallel to the axial direction of the frame 12 when installed to the valve 10) between the first coupling member 314*b* and the leaflet tabs 132*a*, 132*b* after coupling of the coupling members 314*a*, 314*b* to the free ends 312*a*, 312*b*. Alternatively, the wedge element 318 can be coupled to the first coupling member 314*b* (e.g., via one or more sutures) at a location corresponding to that of the central gap 310 (e.g., a midpoint of the first coupling member 314*b*). Positioning of the wedge element 318 between the splayed portions of the leaflet tabs 132*a*, 132*b* can thus occur simultaneously with the positioning of the first coupling member 314*b*.

Figure 5D:
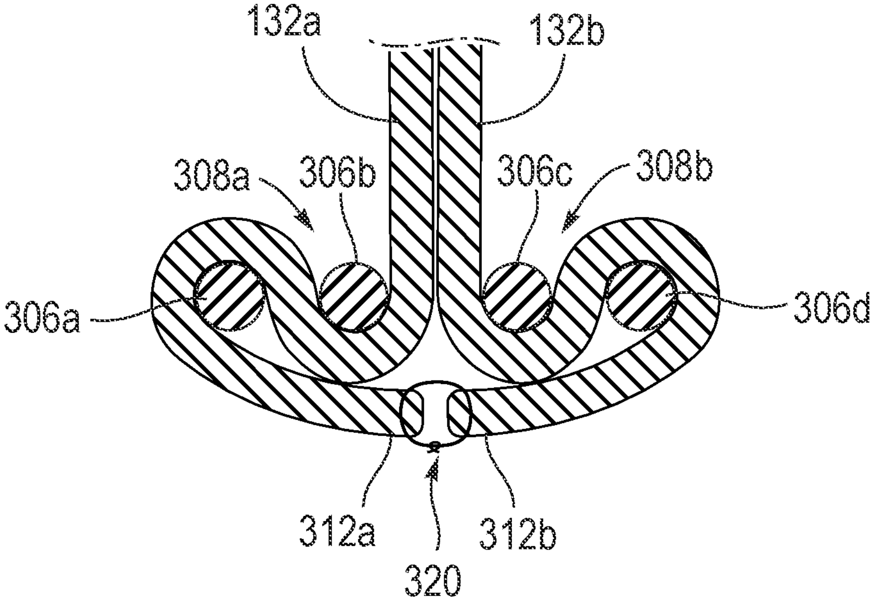
FIG. 5D illustrates a cross-sectional view of another exemplary option for securing free ends of the leaflet tabs assembled to the buckle commissure clamp via direct suturing.

In some embodiments, instead of using coupling members 314*a*, 314*b*, the free ends of the leaflet tabs can be directly coupled together. Indeed, the frictional forces introduced by the serpentine paths through the buckle commissure clamp 302 can enable direct coupling of the free ends together, which direct coupling may otherwise have been unfeasible or unreliable. For example, FIG. 5D illustrates an exemplary coupling of free ends 312*a*, 312*b* of adjacent leaflet tabs 132*a*, 132*b* using one or more sutures 320. In the illustrated configuration, the free ends 312*a*, 312*b* are disposed at the second side of the clamp 302 at locations that overlap with central gap 310 but spaced from each other. Alternatively, the free ends 312*a*, 312*b* can disposed with facing ends abutting, or the free ends 312*a*, 312*b* can overlap each other with sutures 320 stitching together the overlapped portions.

Each leaflet 22 is secured to a pair of buckle commissure clamps 302, one for each leaflet tab 132, with commissures 24 for adjacent leaflets 22 of the valvular structure sharing buckle commissure clamps 302. As described above, a pair of leaflet tabs 132*a*, 132*b* for adjacent leaflets are secured to the buckle commissure clamp 302 to form an assembly. These assemblies can then be secured to respective support members of the prosthetic heart valve 10 to support the valvular structure within the annular frame 12. The prosthetic heart valve 10 may have multiple support members arranged around along a circumferential direction of the annular frame 12, each support member having a respective buckle commissure clamp 302 secured thereto. For example, when the valvular structure has three leaflets 22, three buckle commissure clamps 302 can be used to secure three commissures 24 to a respective one of three support members.

Figure 6:
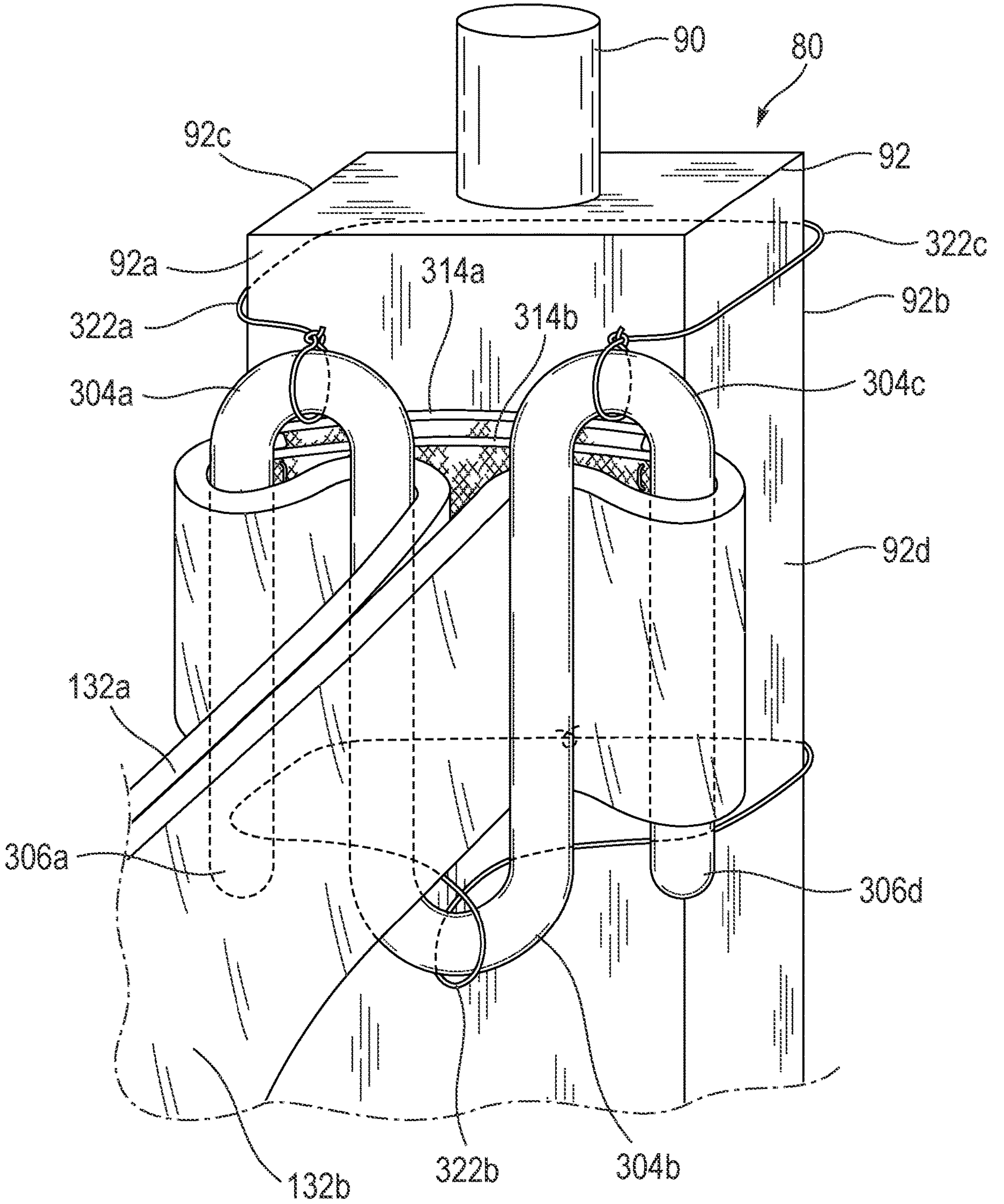
FIG. 6 is a perspective view of the assembly of leaflet tabs and buckle commissure clamp of FIGS. 5A-5B coupled to a support member of an annular frame of the prosthetic heart valve.

FIG. 6 shows an exemplary configuration for securing the leaflet-clamp assembly to a support member of the prosthetic valve, which can be, e.g., an outer member 92 of actuator 80, or a strut or post that is integral to the frame of the prosthetic valve. For example, outer member 92 may have a rectangular cross-section, with an inner surface 92*a*, an outer surface 92*b*, and a pair of side surfaces 92*c*, 92*d* that extend along a radial direction of the annular frame 12. Other cross-sectional shapes for the support member are also possible according to one or more contemplated embodiments, such as, circular or polygonal. The buckle commissure clamp 302 with leaflet tabs 132*a*, 132*b* can be disposed with the second side of the clamp 302 in contact with inner surface 92*a*. One or more attachment members (e.g., sutures, wires, cables, or the like) can then be used to secure the clamp 302 to the outer member 92. For example, one, some, or all of the bent portions 304*a*-304*c* may be coupled to the outer member 92 via one or more attachment members.

In the illustrated embodiment of FIG. 6, each bent portion 304*a*-304*c* of the clamp 302 has a respective suture wrapped around it and at least a portion of the outer member 92. Thus, a first suture 322*a* wraps around bent portion 304*a* and extends around side surface 92*c* to the outer surface 92*b* of the outer member 92. Similarly, a second suture 322*c* wraps around bent portion 304*c* and extends around side surface 92*d* to the outer surface 92*b* of the outer member 92. In some embodiments, first suture 322*a* and second suture 322*c* are different portions of the same suture, such that it extends continuously from bent portion 304*a* to bent portion 304*c* via side surfaces 92*a*, 92*d* and outer surface 92*b*. In other embodiments, first suture 322*a* and second suture 322*c* are separate sutures that can be tied together, for example, at a point along outer surface 92*b*. In FIG. 6, a third suture 322*b* also wraps around bent portion 304*b* and extends around both side surfaces 92*a*, 92*d* to the outer surface 92*b* of the outer member. Opposite ends of the third suture 322*b* can be tied together, for example, at a point along outer surface 92*b*.

In FIG. 6, buckle commissure clamp 302 has an overall width along a circumferential direction of the annular frame that is larger than the corresponding width of facing surface 92*a* of the outer member 92. However, embodiments of the disclosed subject matter are not limited thereto. Rather, clamp 302 can have a width that is smaller or substantially the same as the width of facing surface 92*a* along the circumferential direction of the annular frame 12. The overall width of clamp 302 may be based on the thickness of the base material used to form end portions 306*a*, 306*d* and inner arms 306*b*, 306*c*, as well as the width of the gaps 308*a*, 308*b*, 310. The width of the gaps may be based on an allowable bend radius for forming bent portions 304*a*-304*c* as well as a thickness of the leaflet tabs. As such, the width of central gap 310 may be larger than that of outer gaps 308*a*, 308*b*. Alternatively, the width of each gap may be the same or substantially the same. In some embodiments, the overall width of clamp 302 and the width of the support member may be designed such that the coupled free ends 312*a*, 312*b* are covered by the facing surface 92*a*. Alternatively or additionally, the securing of the assembly to the support member may be such that the free ends 312*a*, 312*b* are further pressed between respective end portion 306*a*, 306*d* and the facing surface 92*a* of the support member, which pressure may further alleviate load applied to sutures or other attachment means coupling the free ends together.

Buckle commissure clamp 302 is illustrated in FIG. 6 as spaced from a proximal edge of outer member 92. However, buckle commissure clamp 302 may be disposed at other locations along the axial direction of the annular frame 12, for example, closer to or farther from the proximal edge of outer member 92. In some embodiments, outer member 92 can include structures for receiving one or more of sutures 322*a*-322*c*, for example, a hole, a recess, or a groove in one or more of surfaces 92*a*-92*d*.

Although FIG. 6 and the discussion above focuses on the support member as a portion of an actuator 80, in particular outer member 92, embodiments of the disclosed subject matter are not limited thereto. Alternatively, support member can instead be a portion of a locking mechanism, or a separate component coupled to the actuator 80 or the locking mechanism. In still another alternative, the support member can be part of the frame (e.g., a strut of the frame) or a component coupled to the frame (e.g., a commissure post separate from or coupled to the actuator 80).

Figure 7:
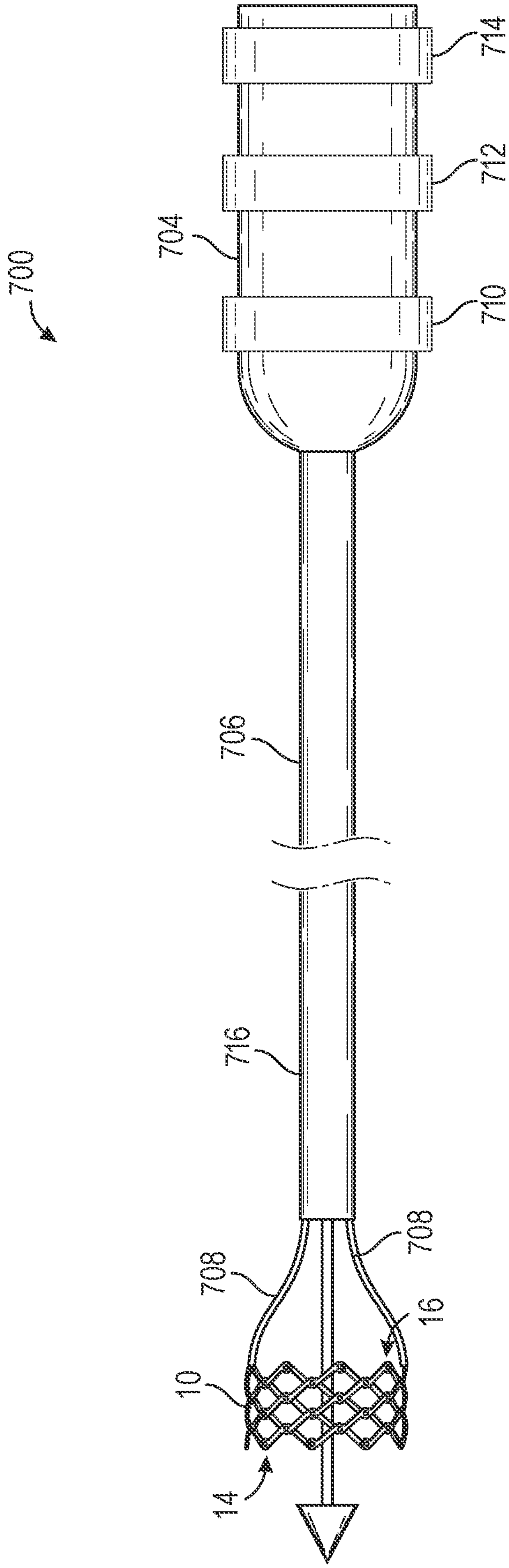
FIG. 7 shows an exemplary prosthetic valve delivery apparatus that can be used for implanting a prosthetic heart valve, according to one or more embodiments of the disclosed subject matter.

FIG. 7 illustrates an exemplary delivery apparatus 700 adapted to deliver a prosthetic heart valve, such as prosthetic heart valve 10 described herein or any other prosthetic heart valve. The prosthetic valve 10 can be releasably coupled to the delivery apparatus 700, such as via a removable coupling between a distal member of an expansion and locking mechanism of the prosthetic valve 10 and a second actuation member of an actuation assembly of the delivery apparatus 700. The prosthetic valve 10 can include a distal end 14 and a proximal end 16, wherein the proximal end 16 is positioned closer to a handle 704 of the delivery apparatus 700 than the distal end 14, and wherein the distal end 14 is positioned farther from the handle 704 than the proximal end 16. It should be understood that the delivery apparatus 700 can be used to implant prosthetic devices other than prosthetic valves, such as stents or grafts.

The delivery apparatus 700 in the illustrated example generally includes the handle 704, a first elongated shaft 706 (which comprises an outer shaft in the illustrated embodiment) extending distally from the handle 704, at least one actuator assembly 708 extending distally through the outer shaft 706. In some examples, a distal end portion 716 of the shaft 706 can be sized to house the prosthetic valve in its radially compressed, delivery state during delivery of the prosthetic valve through the patient's vasculature. In this manner, the distal end portion 716 functions as a delivery sheath or capsule for the prosthetic valve during delivery.

The at least one actuator assembly 708 can be configured to radially expand and/or radially collapse the prosthetic valve 10 when actuated, and may be removably coupled to the prosthetic heart valve 10. Although the illustrated example shows two actuator assemblies 708 for purposes of illustration, it should be understood that one actuator 708 can be provided for each actuator of the prosthetic valve. For example, three actuator assemblies 708 can be provided for a prosthetic valve having three actuators. In other examples, a greater or fewer number of actuator assemblies can be present. The actuator assemblies 708 can be releasably coupled to the prosthetic valve 10. For example, each actuator assembly 708 can be coupled to a respective actuator of the prosthetic valve 10. Each actuator assembly 708 can comprise a support tube or sleeve and an actuator member. In some examples, the actuator assembly 708 also can include a locking tool. When actuated, the actuator assembly can transmit pushing and/or pulling forces to portions of the prosthetic valve to radially expand and collapse the prosthetic valve. The actuator assemblies 708 can be at least partially disposed radially within, and extend axially through, one or more lumens of the outer shaft 706. For example, the actuator assemblies 708 can extend through a central lumen of the shaft 706 or through separate respective lumens formed in the shaft 706.

The handle 704 of the delivery apparatus 700 can include one or more control mechanisms (e.g., knobs or other actuating mechanisms) for controlling different components of the delivery apparatus 700 in order to expand and/or deploy the prosthetic valve 10. For example, in FIG. 7, the handle 704 comprises first, second, and third knobs 710, 712, and 714. The first knob 710 can be a rotatable knob configured to produce axial movement of the outer shaft 706 relative to the prosthetic valve 10 in the distal and/or proximal directions in order to deploy the prosthetic valve from the delivery sheath 716 once the prosthetic valve has been advanced to a location at or adjacent the desired implantation location with the patient's body. For example, rotation of the first knob 710 in a first direction (e.g., clockwise) can retract the sheath 716 proximally relative to the prosthetic valve 10 and rotation of the first knob 710 in a second direction (e.g., counter-clockwise) can advance the sheath 716 distally. In other examples, the first knob 710 can be actuated by sliding or moving the knob 710 axially, such as pulling and/or pushing the knob. In other example, actuation of the first knob 710 (rotation or sliding movement of the knob 710) can produce axial movement of the actuator assemblies 708 (and therefore the prosthetic valve 10) relative to the delivery sheath 716 to advance the prosthetic valve distally from the sheath 716.

The second knob 712 can be a rotatable knob configured to produce radial expansion and/or contraction of the prosthetic valve 10. For example, rotation of the second knob 712 can move the actuator member and the support tube axially relative to one another. Rotation of the second knob 712 in a first direction (e.g., clockwise) can radially expand the prosthetic valve 10 and rotation of the second knob 712 in a second direction (e.g., counter-clockwise) can radially collapse the prosthetic valve 10. In other example, the second knob 712 can be actuated by sliding or moving the knob 712 axially, such as pulling and/or pushing the knob.

The third knob 714 can be a rotatable knob configured to retain the prosthetic heart valve 10 in its expanded configuration. For example, the third knob 714 can be operatively connected to a proximal end portion of the locking tool of each actuator assembly 708. Rotation of the third knob in a first direction (e.g., clockwise) can rotate each locking tool to advance the locking nuts to their distal positions to resist radial compression of the frame of the prosthetic valve. Rotation of the knob 714 in the opposite direction (e.g., counterclockwise) can rotate each locking tool in the opposite direction to decouple each locking tool from the prosthetic valve 10. In other embodiments, the third knob 714 can be actuated by sliding or moving the third knob 714 axially, such as pulling and/or pushing the knob.

Although not shown, in some examples, the handle 704 can include a fourth rotatable knob operative connected to a proximal end portion of each actuator member. The fourth knob can be configured to rotate each actuator member, upon rotation of the knob, to unscrew each actuator member from the proximal portion of a respective actuator. Once the locking tools and the actuator members are uncoupled from the prosthetic valve 10, they can be removed from the patient. Further details regarding construction and operation of a delivery apparatus for delivering and implanting a prosthetic heart valve can be found in U.S. Pat. Nos. 8,652,202, 9,339,384, 9,827,093, 9,867,700, 10,076,638, and 10,806,573, all of which are incorporated herein by reference.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An assembly method for a prosthetic heart valve, the method comprising:

providing a buckle commissure clamp; and coupling tabs of adjacent leaflets to the buckle commissure clamp by passing each leaflet through one or more gaps of the buckle commissure clamp such that each leaflet tab is wrapped around at least a respective portion of the buckle commissure clamp, the leaflets forming a part of a valvular structure for the prosthetic heart valve.

Example 2. The assembly method of any example herein, particularly Example 1, further comprising coupling the buckle commissure clamp to an annular frame of the prosthetic heart valve.

Example 3. The assembly method of any example herein, particularly Example 2, wherein the buckle commissure clamp is coupled to the annular frame via one or more sutures wrapped around one or more portions of the buckle commissure clamp.

Example 4. The assembly method of any example herein, particularly any one of Examples 1-3, wherein the coupling tabs of adjacent leaflets to the buckle commissure clamp comprises wrapping each leaflet tab around multiple portions of the buckle commissure clamp.

Example 5. The assembly method of any example herein, particularly any one of Examples 1-4, wherein:

the buckle commissure clamp comprises first and second arms, first and second end portions, and first, second, and third bent portions, the first and second arms are connected together by the third bent portion at a second end of the buckle commissure clamp, the first and second arms and the third bent portion define a central gap therebetween that opens to a first end of the buckle commissure clamp, the first end portion is connected to the first arm by the first bent portion, the second end portion is connected to the second arm by the second bent portion, the first end portion, the first arm, and the first bent portion define a first gap therebetween that opens to the second end of the buckle commissure clamp, and the second end portion, the second arm, and the second bent portion define a second gap therebetween that opens to the second end of the buckle commissure clamp.

Example 6. The assembly method of any example herein, particularly Example 5, wherein the first and second arms and the first and second end portions are substantially straight members, and the buckle commissure clamp has a W-shape or M-shape.

Example 7. The assembly method of any example herein, particularly any one of Examples 5-6, wherein:

the first and second arms and the first and second end portions are substantially coplanar;

the first and second arms and the first and second end portions are substantially parallel to each other; or both of the above.

Example 8. The assembly method of any example herein, particularly any one of Example 5-7, wherein the providing the buckle commissure clamp comprises bending a single piece of wire at its center to form the third bent portion, and further bending the wire at midpoints between respective ends of the wire and the central bent portion to form the first and second bent portions.

Example 9. The assembly method of any example herein, particularly any one of Examples 5-8, wherein the buckle commissure clamp is coupled to the annular frame via one or more sutures wrapped around the first portion, the second portion, the third portion, or any combination thereof.

Example 10. The assembly method of any example herein, particularly any one of Examples 5-9, wherein the coupling to the annular frame is such that the first end of the buckle commissure clamp is a proximal end and the second end of the buckle commissure clamp is a distal end.

Example 11. The assembly method of any example herein, particularly any one of Examples 5-9, wherein the coupling to the annular frame is such that the first end of the buckle commissure clamp is a distal end and the second end of the buckle commissure clamp is a proximal end.

Example 12. The assembly method of any example herein, particularly any one of Examples 5-11, wherein the coupling tabs of adjacent leaflets to the buckle commissure clamp comprises wrapping each leaflet tab around multiple portions of the buckle commissure clamp.

Example 13. The assembly method of any example herein, particularly Example 12, wherein the coupling tabs of adjacent leaflets to the buckle commissure clamp comprises:

(a) passing a first leaflet tab of the adjacent leaflets from a first side of the buckle commissure clamp through the central gap to a second side of the buckle commissure clamp;

(b) after (a), passing the first leaflet tab from the second side of the buckle commissure clamp through the first gap to the first side of the buckle commissure clamp, such that a portion of the first leaflet tab wraps around a portion of the first arm;

(c) after (b), passing the first leaflet tab from the first side around an outer edge of the buckle commissure clamp to the second side, such that another portion of the first leaflet tab wraps around a portion of the first end portion of the buckle commissure clamp;

(d) passing a second leaflet tab of the adjacent leaflets from the first side of the buckle commissure clamp through the central gap to the second side of the buckle commissure clamp;

(e) after (d), passing the second leaflet tab from the second side of the buckle commissure clamp through the second gap to the first side of the buckle commissure clamp, such that a portion of the second leaflet tab wraps around a portion of the second arm; and (f) after (e), passing the second leaflet tab from the first side around an opposite outer edge of the buckle commissure clamp to the second side, such that another portion of the second leaflet tab wraps around a portion of the second end portion of the buckle commissure clamp.

Example 14. The assembly method of any example herein, particularly Example 13, wherein the coupling tabs of adjacent leaflets to the buckle commissure clamp further comprises:

after (c) and (f), coupling respective free ends of the first and second leaflet tabs to each other.

Example 15. The assembly method of any example herein, particularly Example 14, wherein the coupling respective free ends is via one or more sutures.

Example 16. The assembly method of any example herein, particularly Example 13, wherein the coupling tabs of adjacent leaflets to the buckle commissure clamp further comprises:

after (c) and (f), disposing a coupling member on the second side of the buckle commissure clamp such that free ends of the first and second leaflet tabs are in contact with the coupling member; and coupling the free ends of the first and second leaflet tabs to the coupling member via one or more sutures.

Example 17. The assembly method of any example herein, particularly Example 16, further comprising:

providing a wedge adjacent to the central gap of the buckle commissure clamp and between the first and second leaflet tabs and the coupling member along a direction from the first side to the second side of the buckle commissure clamp.

Example 18. The assembly method of any example herein, particularly any Example 17, wherein the providing the wedge comprises sliding the wedge along a direction from the first end to the second end of the buckle commissure clamp, such that the wedge is inserted between the first side of the buckle commissure clamp and a splayed portion of the first and second leaflet tabs at the central gap.

Example 19. The assembly method of any example herein, particularly Example 17, wherein the providing the wedge comprises attaching the wedge to the coupling member prior to the disposing the coupling member on the second side of the buckle commissure clamp.

Example 20. The assembly method of any example herein, particularly Example 13, wherein (a) and (d) are performed simultaneously with the first and second leaflet tabs disposed together.

Example 21. The assembly method of any example herein, particularly any one of Examples 1-20, wherein:

the buckle commissure clamp is coupled to the annular frame via attachment to a support member that is part of or coupled to the annular frame.

Example 22. The assembly method of any example herein, particularly Example 21, wherein the support member comprises a portion of an actuator or locking mechanism of the prosthetic heart valve or is coupled to the actuator or locking mechanism of the prosthetic heart valve.

Example 23. The assembly method of any example herein, particularly Example 21, wherein the support member comprises a strut or post that is integral with the annular frame.

Example 24. A prosthetic heart valve, comprising:

a frame that is radially collapsible and expandable between a radially-compressed configuration and a radially-expanded configuration, the frame having an inflow end and an outflow end separated from the inflow end along an axial direction of the frame, the frame comprising a plurality of support posts; and a valvular structure supported within the annular frame and comprising a plurality of leaflets, each leaflet having a pair of tabs, the tabs of adjacent leaflets being coupled together using a buckle commissure clamp to form a commissure tab assembly, wherein there is one support post for each commissure tab assembly, and each commissure tab assembly is coupled to the respective support post according to the method of any one of Examples 1-23.

Example 25. A prosthetic heart valve comprising:

a frame that is radially collapsible and expandable between a radially-compressed configuration and a radially-expanded configuration, the frame having an inflow end and an outflow end separated from the inflow end along an axial direction of the frame;

a plurality of buckle commissure clamps coupled to the frame, each buckle commissure clamp having one or more gaps; and a valvular structure formed by a leaflet assembly, the leaflet assembly comprising a plurality of leaflets, each leaflet having a pair of tabs, each leaflet tab being coupled to a respective one of the buckle commissure clamps by being wrapped around at least a portion of the buckle commissure clamp.

Example 26. The prosthetic heart valve of any example herein, particularly any one of Examples 24-25, wherein:

each buckle commissure clamp comprises first and second arms, first and second end portions, and first, second, and third bent portions, the first and second arms are connected together by the third bent portion at a second end of the buckle commissure clamp, the first and second arms and the third bent portion define a central gap therebetween that opens to a first end of the buckle commissure clamp, the first end portion is connected to the first arm by the first bent portion, the second end portion is connected to the second arm by the second bent portion, the first end portion, the first arm, and the first bent portion define a first gap therebetween that opens to the second end of the buckle commissure clamp, and the second end portion, the second arm, and the second bent portion define a second gap therebetween that opens to the second end of the buckle commissure clamp.

Example 27. The prosthetic heart valve of any example herein, particularly Example 26, wherein:

for each buckle commissure clamp, the respective first and second arms and the respective first and second end portions are substantially straight members, and each buckle commissure clamp has a W-shape or M-shape in a view along a radial direction of the annular frame.

Example 28. The prosthetic heart valve of any example herein, particularly any one of Examples 26-27, wherein, for each buckle commissure clamp:

the respective first and second arms and the respective first and second end portions are substantially co-planar;

the respective first and second arms and the respective first and second end portions are substantially parallel to each other; or both of the above.

Example 29. The prosthetic heart valve of any example herein, particularly any one of Examples 26-28, wherein, for each buckle commissure clamp, the respective first and second arms and the respective first and second end portions extend along respective directions parallel to the axial direction of the frame.

Example 30. The prosthetic heart valve of any example herein, particularly any one of Examples 26-29, wherein, for each buckle commissure clamp, the respective first end is closer to the outflow end of the frame than the inflow end of the frame, and the respective second end is closer to the inflow end of the frame than the outflow end of the frame.

Example 31. The prosthetic heart valve of any example herein, particularly any one of Examples 26-29, wherein, for each buckle commissure clamp, the respective first end is closer to the inflow end of the frame than the outflow end of the frame, and the respective second end is closer to the outflow end of the frame than the inflow end of the frame.

Example 32. The prosthetic heart valve of any example herein, particularly any one of Examples 26-31, wherein each buckle commissure clamp is coupled to the frame via one or more sutures wrapped around the first bent portion, the second portion, the third bent portion, or any combination thereof.

Example 33. The prosthetic heart valve of any example herein, particularly any one of Examples 24-32, wherein each leaflet tab is wrapped around multiple portions of the respective buckle commissure clamp.

Example 34. The prosthetic heart valve of any example herein, particularly any one of Examples 26-33, wherein, for each buckle commissure clamp:

a first leaflet tab coupled to said buckle commissure clamp follows a serpentine path through the central gap and the first gap to wrap around portions of the first arm and the first end portion; and a second leaflet tab coupled to said buckle commissure clamp follows another serpentine path through the central gap and the second gap to wrap around portions of the second arm and the second end portion.

Example 35. The prosthetic heart valve of any example herein, particularly Example 34, wherein, for each buckle commissure clamp:

the first and second leaflet tabs extend through the central gap from a first side of said buckle commissure clamp to a second side of the buckle commissure clamp; and free ends of the first and second leaflet tabs at said second side are coupled to each other.

Example 36. The prosthetic heart valve of any example herein, particularly Example 35, wherein the free ends of the first and second leaflet tabs are coupled together using one or more sutures.

Example 37. The prosthetic heart valve of any example herein, particularly Example 34, wherein, for each buckle commissure clamp:

the first and second leaflet tabs extend through the central gap from a first side of said buckle commissure clamp to a second side of the buckle commissure clamp; and one or more coupling members extend between and are attached to respective ends of the first and second leaflet tabs at the second side of the buckle commissure clamp.

Example 38. The prosthetic heart valve of any example herein, particularly Example 37, wherein the one or more coupling members are attached to the first and second leaflet tabs by one or more sutures.

Example 39. The prosthetic heart valve of any example herein, particularly any one of Examples 37-38, for each buckle commissure clamp, a wedge is disposed adjacent to the central gap between the first and second leaflet tabs and the coupling member along a radial direction of the annular frame.

Example 40. The prosthetic heart valve of any example herein, particularly Example 39, wherein the wedge is attached to the coupling member.

Example 41. The prosthetic heart valve of any example herein, particularly any one of Examples 24-40, wherein, for each buckle commissure clamp, ends of the first and second leaflet tabs are disposed between the respective buckle commissure clamp and the frame along a radial direction of the frame.

Example 42. The prosthetic heart valve of any example herein, particularly any one of Examples 24-41, wherein each buckle commissure clamp is coupled to the frame by attachment to a respective support member that is part of or coupled to the frame.

Example 43. The prosthetic heart valve of any example herein, particularly Example 42, wherein the support member comprises a portion of an actuator or a locking mechanism of the frame.

Example 44. The prosthetic heart valve of any example herein, particularly Example 42, wherein the support member is coupled to an actuator or locking mechanism of the frame.

Example 45. The prosthetic heart valve of any example herein, particularly Example 42, wherein the support member comprises a strut or post integral with the frame.

Example 46. The prosthetic heart valve of any example herein, particularly any one of Examples 24-45, wherein each buckle commissure clamp has rounded or smooth surfaces that contact portions of the leaflet tabs coupled to the buckle commissure clamp.

Example 47. The prosthetic heart valve of any example herein, particularly any one of Examples 24-46, wherein the valvular structure is a bicuspid structure with two leaflets and two commissure tab assemblies, and the valvular structure is coupled to the frame via the commissure tab assemblies on diametrically opposite sides of the frame from each other.

Example 48. The prosthetic heart valve of any example herein, particularly any one of Examples 24-46, wherein the valvular structure is a tricuspid structure with three leaflets and three commissure tab assemblies, and the valvular structure is coupled to the frame via the three commissure tab assemblies equally spaced along the circumferential direction of the frame.

Example 49. The prosthetic heart valve of any example herein, particularly any one of Examples 24-48, wherein the frame comprises an annular frame.

Example 50. The prosthetic heart valve of any example herein, particularly any one of Examples 24-49, wherein the frame is formed of a plastically-expandable material or a self-expanding material.

Example 51. The prosthetic heart valve of any example herein, particularly any one of Examples 24-50, wherein the frame comprises an array of angled struts connected together by one or more pivot joints.

Example 52. The prosthetic heart valve of any example herein, particularly any one of Examples 24-51, wherein the prosthetic heart valve is constructed for implantation in an existing heart valve within a patient.

Example 53. The prosthetic heart valve of any example herein, particularly any one of Examples 24-52, wherein the prosthetic heart valve is constructed for implantation at an aortic position, a mitral position, a tricuspid position, or a pulmonary position.

Example 54. A preassembly for attachment to a frame of a prosthetic heart valve, the preassembly comprising:

- a plurality of buckle commissure clamps, each buckle commissure clamp having one or more gaps; and
- a valvular structure formed by a leaflet assembly, the leaflet assembly comprising a plurality of leaflets, each leaflet having a pair of tabs, each leaflet tab being coupled to a respective one of the buckle commissure clamps by being wrapped around at least a portion of the buckle commissure clamp.

Example 55. The preassembly of any example herein, particularly Examples 54, wherein:

- each buckle commissure clamp comprises first and second arms, first and second end portions, and first, second, and third bent portions,
- the first and second arms are connected together by the third bent portion at a second end of the buckle commissure clamp,
- the first and second arms and the third bent portion define a central gap therebetween that opens to a first end of the buckle commissure clamp,
- the first end portion is connected to the first arm by the first bent portion,
- the second end portion is connected to the second arm by the second bent portion,
- the first end portion, the first arm, and the first bent portion define a first gap therebetween that opens to the second end of the buckle commissure clamp, and
- the second end portion, the second arm, and the second bent portion define a second gap therebetween that opens to the second end of the buckle commissure clamp.

Example 56. The preassembly of any example herein, particularly Example 55, wherein:

- for each buckle commissure clamp, the respective first and second arms and the respective first and second end portions are substantially straight members, and
- each buckle commissure clamp has a W-shape or M-shape in a side view.

Example 57. The preassembly of any example herein, particularly any one of Examples 55-56, wherein, for each buckle commissure clamp, the respective first and second arms and the respective first and second end portions are substantially co-planar.

Example 58. The preassembly of any example herein, particularly any one of Examples 55-57, wherein, for each buckle commissure clamp, the respective first and second arms and the respective first and second end portions are substantially parallel to each other.

Example 59. The preassembly of any example herein, particularly any one of Examples 54-58, wherein each leaflet tab is wrapped around multiple portions of the respective buckle commissure clamp.

Example 60. The preassembly of any example herein, particularly Example 59, wherein, for each buckle commissure clamp:

- a first leaflet tab coupled to said buckle commissure clamp follows a serpentine path through the central gap and the first gap to wrap around portions of the first arm and the first end portion; and
- a second leaflet tab coupled to said buckle commissure clamp follows another serpentine path through the central gap and the second gap to wrap around portions of the second arm and the second end portion.

Example 61. The preassembly of any example herein, particularly Example 60, wherein, for each buckle commissure clamp:

the first and second leaflet tabs extend through the central gap from a first side of said buckle commissure clamp to a second side of the buckle commissure clamp; and free ends of the first and second leaflet tabs at said second side are coupled to each other.

Example 62. The preassembly of any example herein, particularly Example 61, wherein the free ends of the first and second leaflet tabs are coupled together using one or more sutures.

Example 63. The preassembly of any example herein, particularly Example 60, wherein, for each buckle commissure clamp:

the first and second leaflet tabs extend through the central gap from a first side of said buckle commissure clamp to a second side of the buckle commissure clamp; and one or more coupling members extend between and are attached to respective ends of the first and second leaflet tabs at the second side of the commissure clamp.

Example 64. The preassembly of any example herein, particularly Example 63, wherein the one or more coupling members are attached to the first and second leaflet tabs by one or more sutures.

Example 65. The preassembly of any example herein, particularly any one of Examples 63-64, wherein for each buckle commissure clamp, a respective wedge is disposed adjacent to the central gap between the pair of leaflet tabs and the coupling member along a radial direction of the frame.

Example 66. The preassembly of any example herein, particularly Example 65, wherein the wedge is attached to the coupling member.

Example 67. The preassembly of any example herein, particularly any one of Examples 54-66, wherein the leaflet assembly comprises three leaflets, and the preassembly has three buckle commissure clamps.

Example 68. A prosthetic heart valve, comprising:

a frame that is radially collapsible and expandable between a radially-compressed configuration and a radially-expanded configuration, the frame having an inflow end and an outflow end separated from the inflow end along an axial direction of the frame, the frame comprising a plurality of support posts; and the preassembly of any one of Examples 54-67 coupled to the support posts of the frame.

Example 69. An assembly, comprising:

a delivery apparatus comprising an elongated shaft; and the prosthetic heart valve of any example herein, particularly any one of Examples 1-53 and 68, the prosthetic heart valve being mounted on or in the elongated shaft in the radially-compressed configuration for delivery into a patient's body.

Example 70. A method of implanting a prosthetic heart valve in a patient's body, the method comprising:

inserting a distal end of a delivery apparatus into vasculature of a patient, the delivery apparatus comprising an elongated shaft, a prosthetic heart valve being releasably mounted in the radially-compressed configuration on the elongated shaft of the delivery apparatus, the prosthetic heart valve being of any example herein, particularly any one of Examples 1-53 and 68;

advancing the prosthetic heart valve to a desired implantation site; and using the delivery apparatus to expand the prosthetic heart valve to the radially-expanded configuration, thereby implanting the prosthetic heart valve at the desired implantation site.

Example 71. A method of implanting a prosthetic heart valve in a patient's body, the method comprising:

inserting a distal end of a delivery apparatus into vasculature of a patient, the delivery apparatus comprising an elongated shaft, a prosthetic heart valve being releasably mounted in the radially-compressed configuration on the elongated shaft of the delivery apparatus, the prosthetic heart valve being of any example herein, particularly any one of Examples 1-53 and 68;

advancing the prosthetic heart valve to a desired implantation site; and deploying the prosthetic heart valve from the delivery apparatus such that the prosthetic heart valve self-expands to the radially-expanded configuration, thereby implanting the prosthetic heart valve at the desired implantation site.

Example 72. The method of any example herein, particularly any one of Examples 70-71, wherein the advancing to the desired implantation site employs transfemoral, transventricular, transapical, or transseptal approaches.

CONCLUSION

All features described herein are independent of one another and, except where structurally impossible, can be used in combination with any other feature described herein. In view of the many possible embodiments to which the principles of the disclosed technology may be applied, it should be recognized that the illustrated embodiments are only preferred examples and should not be taken as limiting the scope of the disclosed technology. Rather, the scope is defined by the following claims. We therefore claim all that comes within the scope and spirit of these claims.

The invention claimed is:

1. A prosthetic heart valve comprising:

a frame that is radially collapsible and expandable between a radially-compressed configuration and a radially-expanded configuration, the frame having an inflow end and an outflow end separated from the inflow end along an axial direction of the frame;

a plurality of buckle commissure clamps coupled to the frame, each buckle commissure clamp having one or more gaps; and a valvular structure formed by a leaflet assembly, the leaflet assembly comprising a plurality of leaflets, each leaflet having a pair of tabs, each leaflet tab being coupled to a respective one of the buckle commissure clamps by being wrapped around at least a portion of the buckle commissure clamp, wherein each buckle commissure clamp comprises first and second arms, first and second end portions, and first, second, and third bent portions, the first and second arms are connected together by the third bent portion at a second end of the buckle commissure clamp, the first and second arms and the third bent portion define a central gap therebetween that opens to a first end of the buckle commissure clamp, the first end portion is connected to the first arm by the first bent portion, the second end portion is connected to the second arm by the second bent portion, the first end portion, the first arm, and the first bent portion define a first gap therebetween that opens to the second end of the buckle commissure clamp, and the second end portion, the second arm, and the second bent portion define a second gap therebetween that opens to the second end of the buckle commissure clamp, and wherein each buckle commissure clamp has a W-shape or M-shape in a view along a radial direction of the frame.

2. The prosthetic heart valve of claim 1, wherein for each buckle commissure clamp, the respective first and second arms and the respective first and second end portions are substantially straight members.

3. The prosthetic heart valve of claim 1, wherein, for each buckle commissure clamp:

the respective first and second arms and the respective first and second end portions are substantially co-planar;

the respective first and second arms and the respective first and second end portions are substantially parallel to each other; or the respective first and second arms and the respective first and second end portions are substantially co-planar and parallel to each other.

4. A prosthetic heart valve comprising:

a frame that is radially collapsible and expandable between a radially-compressed configuration and a radially-expanded configuration, the frame having an inflow end and an outflow end separated from the inflow end along an axial direction of the frame;

a plurality of buckle commissure clamps coupled to the frame, each buckle commissure clamp having one or more gaps; and a valvular structure formed by a leaflet assembly, the leaflet assembly comprising a plurality of leaflets, each leaflet having a pair of tabs, each leaflet tab being coupled to a respective one of the buckle commissure clamps by being wrapped around at least a portion of the buckle commissure clamp, wherein each buckle commissure clamp comprises first and second arms, first and second end portions, and first, second, and third bent portions, the first and second arms are connected together by the third bent portion at a second end of the buckle commissure clamp, the first and second arms and the third bent portion define a central gap therebetween that opens to a first end of the buckle commissure clamp, the first end portion is connected to the first arm by the first bent portion, the second end portion is connected to the second arm by the second bent portion, the first end portion, the first arm, and the first bent portion define a first gap therebetween that opens to the second end of the buckle commissure clamp, and the second end portion, the second arm, and the second bent portion define a second gap therebetween that opens to the second end of the buckle commissure clamp, and wherein, for each buckle commissure clamp, the respective first and second arms and the respective first and second end portions extend along respective directions parallel to the axial direction of the frame.

5. The prosthetic heart valve of claim 1, wherein, for each buckle commissure clamp, the respective first end is closer to the outflow end of the frame than the inflow end of the frame, and the respective second end is closer to the inflow end of the frame than the outflow end of the frame.

6. The prosthetic heart valve of claim 1, wherein, for each buckle commissure clamp, the respective first end is closer to the inflow end of the frame than the outflow end of the frame, and the respective second end is closer to the outflow end of the frame than the inflow end of the frame.

7. The prosthetic heart valve of claim 1, wherein each buckle commissure clamp is coupled to the frame via one or more sutures wrapped around the first bent portion, the second portion, the third bent portion, or any combination thereof.

8. The prosthetic heart valve of claim 1, wherein each leaflet tab is wrapped around multiple portions of the respective buckle commissure clamp.

9. The prosthetic heart valve of claim 1, wherein, for each buckle commissure clamp:

a first leaflet tab coupled to said buckle commissure clamp follows a serpentine path through the central gap from a first side of said buckle commissure clamp to a second side of said buckle commissure clamp, and then through the first gap from the second side of said buckle commissure clamp to the first side of said buckle commissure clamp to wrap around portions of the first arm and the first end portion; and a second leaflet tab coupled to said buckle commissure clamp follows another serpentine path through the central gap from the first side of said buckle commissure clamp to the second side of said buckle commissure clamp, and then through the second gap from the second side of said buckle commissure clamp to the first side of said buckle commissure clamp to wrap around portions of the second arm and the second end portion.

10. The prosthetic heart valve of claim 1, wherein, for each buckle commissure clamp, ends of the first and second leaflet tabs are disposed between the respective buckle commissure clamp and the frame along a radial direction of the frame.

11. The prosthetic heart valve of claim 1, wherein each buckle commissure clamp is coupled to the frame by attachment to a respective support member that is part of or coupled to the frame.

12. The prosthetic heart valve of claim 11, wherein the support member comprises a portion of an actuator or a locking mechanism of the frame, or the support member is coupled to an actuator or locking mechanism of the frame.

13. The prosthetic heart valve of claim 11, wherein the support member comprises a strut or post integral with the frame.

14. A prosthetic heart valve comprising:

a frame that is radially collapsible and expandable between a radially-compressed configuration and a radially-expanded configuration, the frame having an inflow end and an outflow end separated from the inflow end along an axial direction of the frame;

a plurality of buckle commissure clamps coupled to the frame, each buckle commissure clamp having one or more gaps; and a valvular structure formed by a leaflet assembly, the leaflet assembly comprising a plurality of leaflets, each leaflet having a pair of tabs, each leaflet tab being coupled to a respective one of the buckle commissure clamps by being wrapped around at least a portion of the buckle commissure clamp, wherein each buckle commissure clamp comprises first and second arms, first and second end portions, and first, second, and third bent portions, the first and second arms are connected together by the third bent portion at a second end of the buckle commissure clamp, the first and second arms and the third bent portion define a central gap therebetween that opens to a first end of the buckle commissure clamp, the first end portion is connected to the first arm by the first bent portion, the second end portion is connected to the second arm by the second bent portion, the first end portion, the first arm, and the first bent portion define a first gap therebetween that opens to the second end of the buckle commissure clamp, and the second end portion, the second arm, and the second bent portion define a second gap therebetween that opens to the second end of the buckle commissure clamp, and wherein, for each buckle commissure clamp:

the first and second leaflet tabs extend through the central gap from a first side of said buckle commissure clamp to a second side of the buckle commissure clamp; and free ends of the first and second leaflet tabs at said second side are coupled to each other.

15. The prosthetic heart valve of claim 14, wherein the free ends of the first and second leaflet tabs are coupled together using one or more sutures.

16. A prosthetic heart valve comprising:

a frame that is radially collapsible and expandable between a radially-compressed configuration and a radially-expanded configuration, the frame having an inflow end and an outflow end separated from the inflow end along an axial direction of the frame;

a plurality of buckle commissure clamps coupled to the frame, each buckle commissure clamp having one or more gaps; and a valvular structure formed by a leaflet assembly, the leaflet assembly comprising a plurality of leaflets, each leaflet having a pair of tabs, each leaflet tab being coupled to a respective one of the buckle commissure clamps by being wrapped around at least a portion of the buckle commissure clamp, wherein each buckle commissure clamp comprises first and second arms, first and second end portions, and first, second, and third bent portions, the first and second arms are connected together by the third bent portion at a second end of the buckle commissure clamp, the first and second arms and the third bent portion define a central gap therebetween that opens to a first end of the buckle commissure clamp, the first end portion is connected to the first arm by the first bent portion, the second end portion is connected to the second arm by the second bent portion, the first end portion, the first arm, and the first bent portion define a first gap therebetween that opens to the second end of the buckle commissure clamp, and the second end portion, the second arm, and the second bent portion define a second gap therebetween that opens to the second end of the buckle commissure clamp, and wherein, for each buckle commissure clamp:

the first and second leaflet tabs extend through the central gap from a first side of said buckle commissure clamp to a second side of the buckle commissure clamp; and one or more coupling members extend between and are attached to respective ends of the first and second leaflet tabs at the second side of the buckle commissure clamp.

17. The prosthetic heart valve of claim 16, wherein the one or more coupling members are attached to the first and second leaflet tabs by one or more sutures.

18. The prosthetic heart valve of claim 16, for each buckle commissure clamp, a wedge is disposed adjacent to the central gap between the first and second leaflet tabs and the coupling member along a radial direction of the frame.

19. The prosthetic heart valve of claim 18, wherein the wedge is attached to the coupling member.

* * * * *